(12) United States Patent
Conte et al.

(10) Patent No.: US 8,012,982 B2
(45) Date of Patent: Sep. 6, 2011

(54) MODULATORS OF HCV REPLICATION

(75) Inventors: Immacolata Conte, Rome (IT); Caterina Ercolani, Rome (IT); Claudio Giuliano, Rome (IT); Giovanni Migliaccio, Rome (IT); Gessica Filocamo, legal representative, Rome (IT); Veronica Suriano, legal representative, Rome (IT); Ian Stansfield, Ariccia (IT)

(73) Assignee: Istituto di Ricerche Biologia Molecolare P. Angeletti SpA, Rome (IT)

( * ) Notice: Subject to any disclaimer, the term of this patent is extended or adjusted under 35 U.S.C. 154(b) by 516 days.

(21) Appl. No.: 11/664,580

(22) PCT Filed: Sep. 29, 2005

(86) PCT No.: PCT/GB2005/050170
§ 371 (c)(1),
(2), (4) Date: Aug. 4, 2008

(87) PCT Pub. No.: WO2006/038039
PCT Pub. Date: Apr. 13, 2006

(65) Prior Publication Data
US 2009/0069344 A1    Mar. 12, 2009

(30) Foreign Application Priority Data
Oct. 1, 2004 (GB) .................. 0421908.5

(51) Int. Cl.
*A61K 31/4965* (2006.01)
*C07D 241/04* (2006.01)
*C07D 295/00* (2006.01)

(52) U.S. Cl. ............. 514/255.01; 514/255.03; 544/383; 544/389; 544/393

(58) Field of Classification Search ............. 514/255.01, 514/255.03; 544/383, 389, 393
See application file for complete search history.

(56) References Cited

U.S. PATENT DOCUMENTS

| | | | |
|---|---|---|---|
| 5,780,480 A | 7/1998 | Wai et al. | |
| 5,854,245 A | 12/1998 | Duggan et al. | |
| 6,451,800 B1 | 9/2002 | Ajito et al. | |
| 6,630,343 B1 | 10/2003 | Bartenschlager | |
| 2004/0133008 A1 | 7/2004 | Inoue et al. | |

FOREIGN PATENT DOCUMENTS

| | | | |
|---|---|---|---|
| EP | 0 277 725 A2 | | 8/1988 |
| EP | 1 176 140 B1 | | 12/2004 |
| WO | WO 97/25323 A1 | | 7/1997 |
| WO | WO 97/31910 | * | 9/1997 |
| WO | WO 97/31910 A1 | | 9/1997 |
| WO | WO 98/00134 | * | 1/1998 |
| WO | WO 98/00134 A1 | | 1/1998 |
| WO | WO 98/00144 A1 | | 1/1998 |
| WO | WO 98/00401 A1 | | 1/1998 |
| WO | WO 99/25323 A1 | | 8/1999 |
| WO | WO 99/38849 A1 | | 8/1999 |
| WO | WO 01/89364 A2 | | 11/2001 |
| WO | WO 02/059321 A2 | | 8/2002 |
| WO | WO 03/047575 A1 | | 6/2003 |
| WO | WO 03/048121 A1 | | 6/2003 |
| WO | WO 03/070174 A2 | | 8/2003 |
| WO | WO 03/076421 A1 | | 9/2003 |
| WO | WO 03/076422 | * | 9/2003 |
| WO | WO 03/076422 A1 | | 9/2003 |
| WO | WO 03/089672 A1 | | 10/2003 |
| WO | WO 2004/039795 A2 | | 5/2004 |

OTHER PUBLICATIONS

Bukh, et al., Mutations hat Permit Efficient Replication of Hepatitis C Virus RNA in Huh-7 Cells Prevent Productive Replication in Chimpanzees, PNAS, vol. 99, No. 22, 14416-14421 (2002).*
David A. Walsh et al., "Synthesis and Antiallergy Activity of N-[2-(Dimethylamino)ethyl]-4-aryl-1-piperazinecarboxamide Derivatives," 33(7) J. Med Chem. 2028-32 (1990).
Annemarie Wasley and Miriam J. Alter, Epidemiology of Hepatitis C: Geographic Differences and Temporal Trends, Seminars in Liver Disease, 20(1) 1-16 (2000).
Sten Iwarson, The Natural Course of Chronic Hepatitis C, FEMS Microbiology Reviews, vol. 14, 201-204 (1994).
Michael C. Kew, Hepatitis C Virus and Hepatocellular Carcinoma, FEMS Microbiology Reviews, vol. 14, 211-220 (1994).
Harvey J. Alter, To C or Not To C: These Are the Questions, Blood, 85(7) 1681-1695 (1995).
V. Lohmann et al., Replication of Subgenomic Hepatitis C Virus RNAs in a Hepatoma Cell Line, Science, vol. 285, 110-113 (1999).
Volker Lohmann et al., Viral and Cellular Determinants of Hepatitis C Virus RNA Replication in Cell Culture, Journal of Virology, 77(5) 3007-3019 (2003).
Ralf Bartenschlager et al., Replication of the Hepatitis C Virus in Cell Culture, Antiviral Research, vol. 60, 91-102 (2003).

(Continued)

*Primary Examiner* — Noble Jarrell
*Assistant Examiner* — Erich Leeser
(74) *Attorney, Agent, or Firm* — Jule M. Lake; Sheldon O. Heber

(57) ABSTRACT

The present invention is directed to compounds of formula (I):

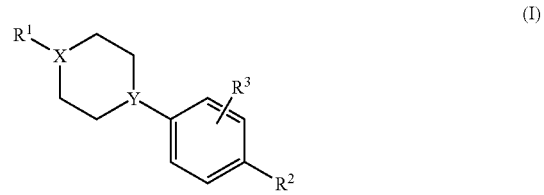

where X, Y, $R^1$, $R^2$ and $R^3$ are defined therein, which can act as modulators of viral replication and/or virus production, especially of the hepatitis C virus (HCV).

7 Claims, 2 Drawing Sheets

OTHER PUBLICATIONS

Caterina Trozzi et al., In Vitro Selection and Characterization of Hepatitis C Virus Serine Protease Variants Resistant to an Active-Site Peptide Inhibitor, Journal of Virology, 77(6) 3669-3679 (2003).

Giovanna Mottola et al., Hepatitis C Virus Nonstructural Proteins Are Localized in a Modified Endoplasmic Reticulum of Cells Expressing Viral Subgenomic Replicons, Virology, vol. 293, 31-43 (2002).

Jay A. Grobler et al., Identification of a Key Determinant of Hepatitis C Virus Cell Culture Adaptation in Domain II of NS3 Helicase, The Journal of Biological Chemistry, 278(19) 16741-16746 (2003).

Laura Pacini et al., Reporter Substrates for Assessing the Activity of the Hepatitis C Virus NS3-4A Serine Protease in Living Cells, Analytical Biochemistry, vol. 331, 46-59 (2004).

Edward M. Murray et al., Persistant Replication of Hepatitis C Virus Replicons Expressing the beta-Lactamase Reporter in Subpopulations of Highly Permissive Huh7 Cells, Journal of Virology, 77(5) 2928-2935 (2003).

Piotr Chomczynski & Nicoletta Sacchi, Single-Step Method of RNA Isolation by Acid Guanidinium Thiocyanate-Phenol-Chloroform Extraction, Analytical Biochemistry, vol. 162, 156-159 (1987).

W. Clark Still et al., Rapid Chromatographic Technique for Preparative Separations with Moderate Resolution, Journal of Organic Chemistry, 43(14) 2923-2925 (1978).

Sachin S. Chaudhari & Krishnacharya G. Adamanchi, Thionyl Chloride-benzotriazole in Methylene Chloride: A Convenient Solution for Conversion of Alcohols and Carboxylic Acids Expeditiously into Alkyl Chlorides and Acid Chlorides by Simple Titration, Synlett, No. 11, 1763-1765 (1999).

Database CA [online], Chemical Abstracts Service, Columbus, Ohio US; XP002371248, retrieved from CA Accession No. 140:406743 abstract, Fujisawa Pharmaceutical Co., Ltd. et al., May 13 2004.

* cited by examiner

A

Compound (Ib) nM

B

MODULATORS OF HCV REPLICATION

CROSS REFERENCE TO RELATED APPLICATIONS

This is a National filing under 35 U.S.C. §371 of PCT/GB2005/050170, filed Sep. 29, 2005, which claims priority from GB 0421908.5, filed Oct. 1, 2004.

BACKGROUND OF THE INVENTION

The present invention is directed to the use of certain compounds which can act as modulators of viral replication and/or virus production, especially of the hepatitis C virus (HCV), in a cell based system.

It is estimated that about 3% of the world's population are infected with the Hepatitis C virus (HCV) (Wasley, et al., 2000, *Semin. Liver Dis.* 20, 1-16). Exposure to HCV results in an overt acute disease in a small percentage of cases, while in most instances the virus establishes a persistent infection that results in chronic hepatitis, liver cirrhosis and liver failure (Iwarson, 1994, *FEMS Microbiol. Rev.* 14, 201-204). In addition, epidemiological surveys indicate an important role of HCV in the pathogenesis of hepatocellular carcinoma (Kew, 1994, *FEMS Microbiol. Rev.* 14, 211-220, Alter, 1995. *Blood* 85, 1681-1695).

Investigating the effects of antiviral compounds on HCV replication is complicated by the absence of a way to reproduce infection in laboratory small animal models as well as in cultivated cells. HCV infects human and chimpanzees, but does not infect small animals such as mice and rats. Similarly, HCV does not efficiently propagate in any cultivated cells or tissues.

Lohmann et al., *Science* 285, 110-113, 1999 disclose a HCV cell culture system where the viral RNA self-replicates in the transfected cells efficiently, and illustrate the ability of a bicistronic HCV subgenomic replicon to replicate in a hepatoma cell line. An HCV replicon is an RNA molecule able to autonomously replicate in a cultured cell and produce detectable levels of one or more HCV proteins.

HCV replicons can thus be used to produce a cell culture replication system providing detectable levels of HCV RNA and HCV protein. In order to replicate efficiently, however, the majority of the available replicons require the presence of adaptive mutations (see for example, Lohmann et al., *J Virol* 77, 3007-3019, 2003).

Adaptive mutations are mutations in HCV RNA that enhance the ability of an HCV replicon to be maintained and expressed in a host cells. Examples of adaptive mutations can be found in U.S. Pat. No. 6,630,343 B1; WO2002059321 A2; WO0189364 A2; Bartenschlager et al., *Antiviral Res.* 60, 91-102, 2003, and references therein.

Certain phenylpiperazine and phenylpiperidine derivatives have been disclosed in the art but none are disclosed as being useful as modulators of viral replication.

Published International application WO 98/00134 (Merck & Co., Inc.) discloses the compounds of formula (A):

X—Y—Z-A-B (A)

wherein X is a 5, 6 or 7 membered aromatic or nonaromatic ring, and Y is a 5 or 6 membered aromatic ring, such as:

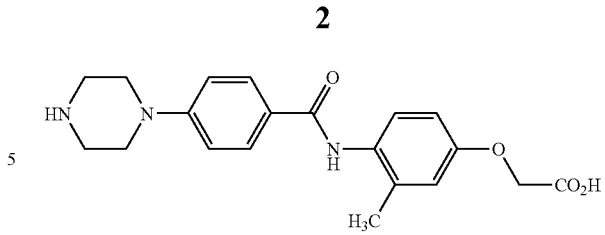

as fibrinogen receptor antagonists.

Published International application WO 03/076422 (Janssen Pharmaceutica N.V.) discloses the sulfonyl derivatives of formula (B):

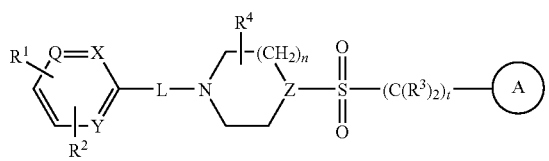

(B)

where A, L, Q, X, Y, Z, $R^1$, $R^2$, $R^3$, $R^4$, n and t are defined therein, as inhibitors of histone deacetylase.

Published International application WO 99/38849 (Meiji Seika Kaisha, Ltd.) discloses the compounds of formula (C):

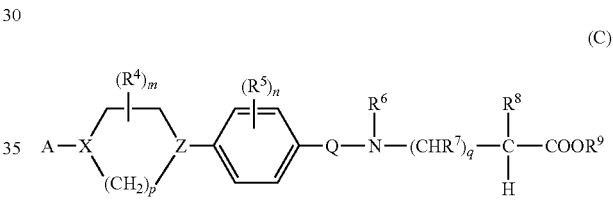

(C)

where A, Q, X, Z, $R^4$, $R^5$, $R^6$, $R^7$, $R^8$, $R^9$, m, n, p and q are defined therein, as integrin αvβ3 antagonists.

Published International application WO 97/25323 (SmithKline Beecham Corporation) discloses the compounds of formula (D):

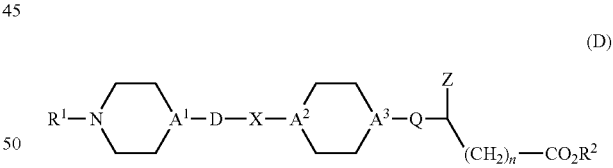

(D)

where $A^1$, $A^2$, $A^3$, D, Q, X, Z, $R^1$, $R^2$ and n are defined therein, as fibrinogen receptor antagonists.

Published European application EP 277725 (A.H. Robins Company, Incorporated) discloses 4-aryl-N-[2-(dialkylamino and heterocyclicamino)alkyl]-1-piperazinecarboxamides of formula (E):

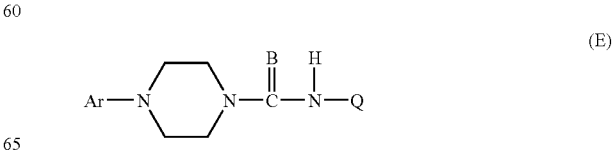

(E)

where B, Ar and Q are defined therein, as antiallergy agents.

BRIEF SUMMARY OF THE INVENTION

It has now surprisingly been found that certain phenylpiperazine and phenylpiperidine derivatives, including certain of the known compounds referred to above, can be used to support replication of HCV RNA in cell culture without the need to introduce adaptive mutations. Such cell culture system is a better mimic of in vivo replication and is useful in supporting replication of naturally occurring HCV sequences and assisting the establishment of HCV viral infection assays in cultured cells and test animals.

In addition, it has also been found that while these compounds have stimulatory effects on the replication of HCV RNA lacking adaptive mutations, at certain concentrations they can also inhibit replication of HCV RNA, in particular of HCV RNAs containing adaptive mutations. Such inhibitors may thus have therapeutic applications to treat individuals infected with HCV.

Thus, in one aspect, the present invention provides the use of a compound of formula (I), or a suitable salt thereof, to modulate the replication of HCV RNA and/or viral production of HCV in a cell, a tissue or an organism.

In a further aspect, the present invention provides a method for modulating the replication of HCV RNA and/or viral production of HCV in a cell, a tissue or an organism comprising administering to the cell, the tissue or the organism a compound of formula (I), or a suitable salt thereof.

The skilled addressee will appreciate that references herein to "modulation" and the like of replication of HCV RNA or viral production of HCV is intended to include the inhibition and enhancement of HCV RNA replication or HCV production.

Thus, in one embodiment, there is provided the use of a compound of formula (I), or a suitable salt thereof, to enhance HCV RNA replication and/or viral production of HCV in a cell.

In a further embodiment, there is provided a method of enhancing HCV RNA replication and/or viral production of HCV in a cultured cell by treating the cell with a compound of formula (I) or a suitable salt thereof.

In a further aspect, the present invention provides a cell culture obtainable by treatment with a compound of formula (I) or a suitable salt thereof.

The skilled addressee will appreciate that references herein to HCV RNA are intended to include sub-genomic replicons and full length HCV RNAs. Full length HCV RNA can be introduced into a cell by transfection of HCV RNA or by inoculating the cell with HCV virus obtained from infected individuals or produced in cell culture.

Enhancing HCV RNA replication in a cell with the compounds of the present invention brings about at least one of the following: an increase in maintenance of HCV RNA replication, an increase in the rate of HCV RNA replication, an increase in HCV RNA expression, an increase in HCV protein expression, and an increase in virus production.

Enhancing replication and expression of HCV RNA in a cell culture system using the compounds of the present invention has a variety of different uses, including being used to study HCV replication and expression, to study HCV and host cell interactions, to produce HCV RNA, to produce HCV proteins, to assist in establishing HCV viral infection in cell culture and to provide a system for measuring the ability of a compound to modulate one or more HCV activities.

In a further aspect, the present invention provides a method of screening a compound for its effect on HCV replication which comprises administration of the compound to a HCV cell culture that has been treated with a compound of formula (I) or a suitable salt thereof.

The compounds described in this invention can be used to produce a cell culture providing detectable levels of HCV RNA and HCV protein in the absence of adaptive mutations that are specific for given cell culture conditions, cell lines or HCV viral isolates. Moreover, the compounds described in the present invention can be exploited to enable replication, in cultivated cells, of HCV RNA with naturally occurring sequences representing different isolates and genotypes.

Thus, in a further aspect, the present invention provides the use of a compound of formula (I) or a suitable salt thereof in the production of a cell culture which has detectable levels of HCV RNA and HCV protein in the absence of adaptive mutations in the HCV RNA.

In a further aspect, the present invention provides a method of producing a cell culture which has detectable levels of HCV RNA in the absence of adaptive mutations in the HCV RNA by:

a) contacting a cell in tissue culture with HCV RNA or HCV virus not carrying adaptive mutations,
b) treating the cell with a compound of formula (I) or a suitable salt thereof,
c) evaluating the treated cell for HCV RNA replication.

In a further aspect, the present invention provides a method for producing a cell culture which has detectable levels of HCV protein in the absence of adaptive mutations in the HCV RNA by:

a) contacting a cell in tissue culture with HCV RNA or HCV virus not carrying adaptive mutations,
b) treating the cell with a compound of formula (I) or a suitable salt thereof,
c) evaluating the treated cell for HCV protein expression.

In a further aspect, the present invention provides a method of producing a cell culture which has detectable levels of virus production in the absence of adaptive mutations by:

a) contacting a cell in tissue culture with HCV RNA or HCV virus not carrying adaptive mutations,
b) treating the cell with a compound of formula (I) or a suitable salt thereof,
c) evaluating the amount of viral particles secreted in the cell medium.

The compounds described in this invention can also be used in combination with selected adaptive mutations present in HCV variants in order to assist the establishment of detectable HCV RNA replication and HCV protein expression in cultivated cells.

Thus, in a further aspect, the present invention provides the use of a compound of formula (I) or a suitable salt thereof in the production of a cell culture which has detectable levels of HCV RNA and HCV protein in the presence of selected adaptive mutations in those cells.

In a further aspect, the present invention provides a method of producing a cell culture which has detectable levels of HCV RNA in the presence of selected adaptive mutations in those cells by:

a) contacting a cell in tissue culture with HCV RNA or HCV virus carrying selected adaptive mutations,
b) treating the cell with a compound of formula (I) or a suitable salt thereof,
c) evaluating the treated cell for HCV RNA replication.

In a further aspect, the present invention provides a method of producing a cell culture which has detectable levels of HCV protein in the presence of selected adaptive mutations in those cells by:

a) contacting a cell in tissue culture with HCV RNA or HCV virus carrying adaptive mutations,
b) treating the cell with a compound of formula (I) or a suitable salt thereof,
c) evaluating the treated cell for HCV protein expression.

In a further aspect, the present invention provides a method of producing a cell culture which has detectable levels of virus production in the presence of adaptive mutations by:
a) contacting a cell in tissue culture with HCV RNA or HCV virus carrying adaptive mutations,
b) treating the cell with a compound of formula (I) or a suitable salt thereof,
c) evaluating the amount of viral particles secreted in the cell medium.

DETAILED DESCRIPTION OF THE INVENTION

Figure 1:
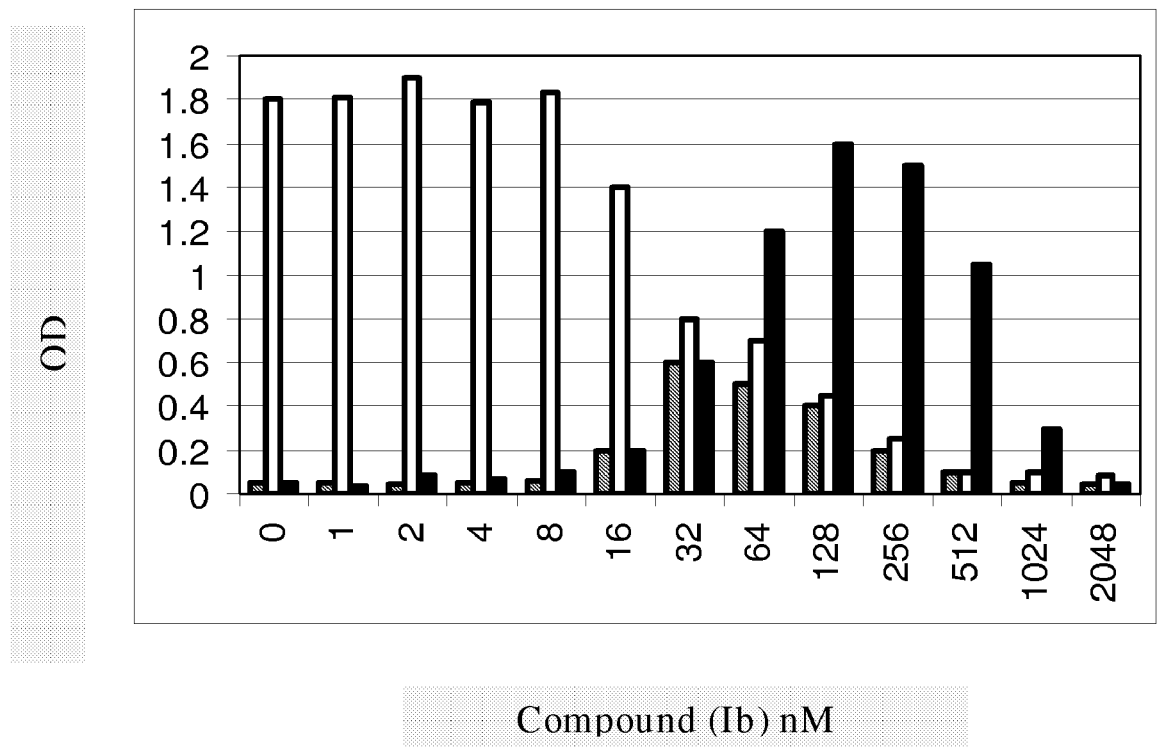
FIG. 1A illustrates dose-dependency of replicon replication with respect to an exemplary compound of the invention.
FIG. 1B shows a Northern blot analysis confirming an activation effect of an exemplary compound of the invention.
Figure 1:
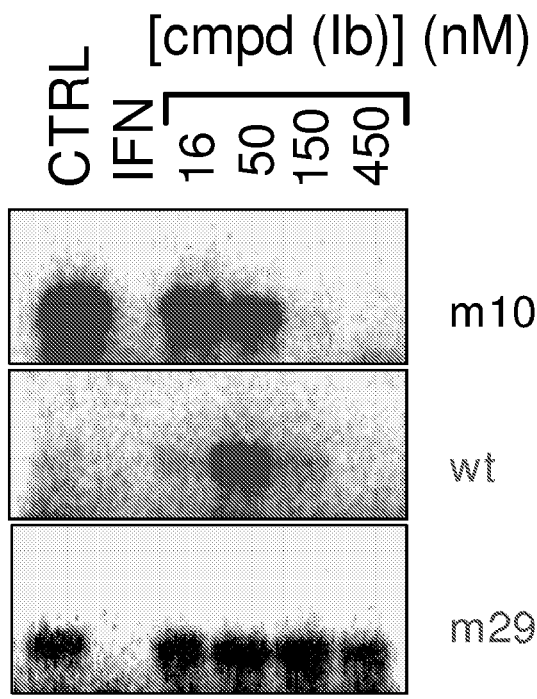

Cell systems suitable for use in the present invention include, but are not restricted to, primary human cells, for example hepatocytes, T-cells, B-cells and foreskin fibroblasts, as well as continuous human cell lines, for example HuH7, HepG2, HUT78, HeLa, 293, HPB-MA, MT-2, MT-2C, and other HTLV-1 and HTLVII infected T-cell lines, Namalawa, Daudi, EBV-transformed LCLs. In addition, cell lines of other species, especially those that are permissive for replication of flaviviruses or pestiviruses, for example SW-13, Vero, BHK-21, COS, PK-15, MBCK, MDCK, Hepa1-6, etc., can be used.

Preferred cell systems are hepatoma cell lines such as Huh-7, Hep3B, HepG2 and HeLa.

The skilled person will appreciate that the uses and methods described herein to modulate HCV RNA replication and/or HCV virus production in cell cultures can be adapted to modulate HCV RNA replication, HCV virus infection and/or HCV virus production in test animals.

Test animals suitable for use in the present invention include mammals such as rodents. Preferred test animals are rodents such as rats and mice.

The presence of replicating HCV RNA can be evaluated by conventional methods such as, for example, RT-PCR, quantitative RT-PCR, Northern blotting, or by measuring the activity and/or expression of an HCV protein or protein encoded by reporter gene engineered into the HCV RNA.

HCV protein expression can be evaluated by conventional methods such as, for example, ELISA assays, Western Immunoblots, or radioactive protein labeling followed by immunoprecipitation assays.

The presence of HCV viral particles secreted in the cell medium can be evaluated by conventional methods, such as, for example, real-time reverse transcription PCR amplification (TaqMan), b-DNA, or by utilizing the cell medium to infect naïve cells or laboratory animals.

The compound of formula (I) is defined as:

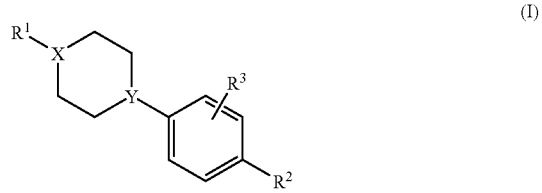

(I)

wherein
X and Y are independently CH or N, with the proviso that X and Y are not both CH;
$R^1$ is $C(O)OR^4$, $C(O)NR^5R^6$, $C(O)R^7$ or $S(O)_2R^8$;
$R^2$ is $C(O)NR^9R^{10}$ or $NR^9C(O)R^{10}$;
$R^3$ is absent or selected from halogen, hydroxy, $C_{1-6}$alkyl and $C_{1-6}$alkoxy;
$R^5$ and $R^9$ are each independently hydrogen, $C_{1-6}$alkyl or $C_{3-8}$cycloalkyl;
$R^4$, $R^6$, $R^7$ and $R^8$ are each independently selected from $C_{1-6}$alkyl, $C_{2-6}$alkenyl, $C_{2-6}$alkynyl, $(CH_2)_{0-3}C_{3-8}$cycloalkyl, $C_{1-6}$alkoxy, $(CH_2)_{0-3}$aryl, $(CH)_2$aryl, $(CH_2)_{0-3}$Oaryl, $(CH_2)_{0-3}$heteroaryl and $(CH_2)_{0-30}$heteroaryl,
optionally substituted by hydroxy, halogen, CN, $CF_3$, $C_{1-4}$alkyl, $C_{1-4}$alkoxy, $(CH_2)_{0-3}NR^{11}C(O)OR^{12}$, $(CH_2)_{0-3}$aryl or $(CH_2)_{0-3}$heteroaryl,
where $R^{11}$ and $R^{12}$ are each independently hydrogen or $C_{1-6}$alkyl;
$R^{10}$ is $(CH_2)_{0-3}$aryl or $(CH_2)_{0-3}$heteroaryl, optionally substituted by halogen, CN, $CF_3$, $C_{1-4}$alkyl, $C_{2-4}$alkenyl, $OR^{13}$, $C(O)R^{13}$, $C(O)OR^{13}$, aryl, $(CH)_2$aryl, $(CH)_2C(O)OR^{13}$ or $NR^{13}R^{14}$,
where $R^{13}$ and $R^{14}$ are each independently hydrogen, $C_{1-4}$alkyl or $(CH_2)_{0-3}$aryl,
and where the optional substituent is further optionally substituted by hydroxy or halogen,
and $R^{10}$ may further be fused to a 5- or 6-membered ring, which ring may be partially or fully unsaturated and which ring may contain one or two N atoms, said ring being optionally substituted by hydroxy,
halogen, $C_{1-4}$alkyl, $C_{1-4}$alkoxy, $C(O)R^{15}$ and $C(O)OR^{15}$,
where $R^{15}$ is $C_{1-4}$alkyl or aryl.

A preferred sub-class of the compound of formula (I) is the compound of formula (II):

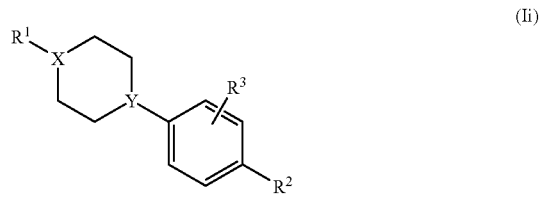

(Ii)

wherein $R^1$ and $R^2$ are as defined in relation to formula (I), and $R^3$ is absent or selected from hydroxy, $C_{1-6}$alkyl and $C_{1-6}$alkoxy.

Preferably, X and Y are both N.
Preferably, $R^1$ is $C(O)OR^4$, $C(O)NR^5R^6$ or $C(O)R^7$, where $R^4$, $R^5$, $R^6$ and $R^7$ are as previously defined. More preferably, $R^1$ is $C(O)OR^4$.
Preferably, $R^4$, $R^6$ and $R^7$ are each independently selected from $C_{1-6}$alkyl, aryl and benzyl, optionally substituted by one or two substituents chosen from fluorine, chlorine, bromine, CN, methyl, methoxy and $CF_3$.

More preferably, $R^4$ is $C_{1-6}$alkyl, most preferably $C_{1-4}$alkyl, especially ethyl, s-butyl and t-butyl.

More preferably, $R^6$ is benzyl, optionally substituted by fluorine, chlorine or methyl.

More preferably, $R^7$ is $(CH_2)_{0-2}C_{5-6}$cycloalkyl, $(CH_2)_{0-2}$aryl or $(CH)_2$aryl where the aryl group, especially when phenyl, is optionally substituted by CN or $CF_3$.

Preferably, $R^5$ is hydrogen.

Preferably, $R^2$ is $C(O)NR^9R^{10}$ where $R^9$ and $R^{10}$ are as previously defined.

Preferably, $R^9$ is hydrogen or methyl. Most preferably, $R^9$ is hydrogen.

Preferably, $R^{10}$ is $(CH_2)_{0-3}$phenyl or heteroaryl, optionally substituted by halogen, hydroxy, CN, $CF_3$, $C_{1-4}$alkyl, $C_{2-4}$alkenyl, $C(O)R^{13}$, $C(O)OR^{13}$ or $(CH)_2$-phenyl, where $R^{13}$ is as hereinbefore defined, and where the optional substituent is further optionally substituted by hydroxy or halogen. More preferably, $R^{10}$ is phenyl, —$CH_2CH_2$phenyl or benzothiazolyl, optionally substituted by halogen, hydroxy, CN, $CF_3$ or

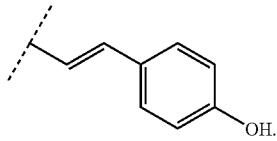

When $R^{10}$ is phenyl or —$CH_2CH_2$phenyl, preferably $R^{10}$ is substituted, most preferably mono-substituted, more preferably at the 4-position.

Preferably, $R^3$ is absent or hydroxy. When $R^3$ is hydroxy, preferably it is attached at a position adjacent to the $R^2$ substituent. Preferably, $R^3$ is absent.

Another preferred sub-class of the compound of formula (I) is the compound of formula (Ia):

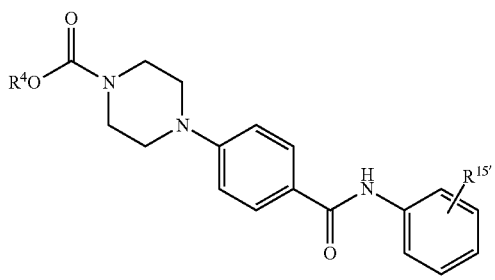

wherein $R^4$ is as defined in relation to formula (I), and —$R^{15'}$ may be absent or is halogen, CN, $CF_3$, $C_{1-4}$alkyl, $C_{2-4}$alkenyl, $OR^{13}$, $C(O)R^{13}$, $C(O)OR^{13}$, aryl, $(CH_2)_2$aryl, $(CH_2)_2C(O)OR^{13}$ or $NR^{13}R^{14}$, optionally substituted by halogen or hydroxy, where $R^{13}$ and $R^{14}$ are as defined in relation to formula (I).

Preferably, $R^4$ is $C_{1-6}$alkyl, $C_{2-6}$alkenyl or $(CH_2)_{0-3}$aryl, optionally substituted by one or two substituents selected from halogen, $C_{1-4}$alkyl, $C_{1-4}$alkoxy and —$CH_2NHC(O)OC_{1-4}$alkyl. More preferably, $R^4$ is ethyl, butyl, pentyl, propenyl, phenyl, benzyl or $(CH_2)$naphthyl. Most preferably, $R^4$ is butyl, particularly t-butyl, or benzyl.

When $R^4$ is benzyl, it is optionally substituted by one or two substituents selected from chlorine, bromine, methyl, methoxy and —$CH_2NHC(O)OCH_3$.

Preferably, $R^{15}$ is halogen, CN, $CF_3$, $C_{2-4}$alkenyl, phenyl, hydroxy, OAc, OBn, $C(O)C_{1-4}$alkyl, $C(O)$phenyl, $C(O)OC_{1-4}$alkyl, $(CH)_2C(O)OC_{1-4}$alkyl, $N(C_{1-4}$alkyl$)_2$ or

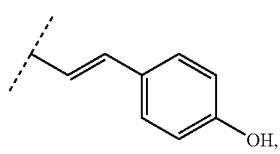

More preferably, $R^{15}$ is bromine, iodine, $CF_3$, vinyl, hydroxy, $C(O)CH_3$, $C(O)OCH_3$, $(CH_2)C(O)OCH_3$, $NMe_2$ or

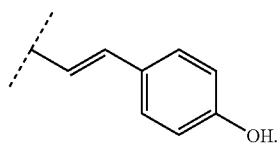

Most preferably, $R^{15}$ is bromine, $CF_3$, hydroxy or

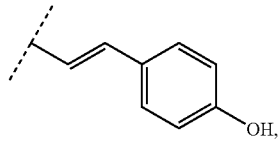

especially hydroxy.

When $R^{15}$ is present, it is preferably at the 3- or 4-position of the phenyl ring, particularly the 4-position.

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl.

As used herein, the term "alkenyl" and "alkynyl" as a group or part of a group means that the group is straight or branched. Examples of suitable alkenyl groups include vinyl and allyl. Suitable alkynyl groups are ethynyl and propargyl.

When used herein, the term "halogen" means fluorine, chlorine, bromine and iodine. Preferred halogens are fluorine and chlorine.

When used herein, the term "aryl" as a group or part of a group means a carbocyclic aromatic ring. Examples of suitable aryl groups include phenyl and naphthyl.

When used herein, the term "heteroaryl" as a group or part of a group means a 5- to 10-membered heteroaromatic ring system containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzimidazolyl, benzothienyl, benzothiazolyl and quinolinyl.

Where a compound or group is described as "optionally substituted", one or more substituents may be present.

Optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of the compound of formula (I) include those named in the Examples and Tables below.

A compound of particular interest is tert-butyl 4-(4-{[(4-hydroxyphenyl)amino]carbonyl}phenyl)piperazine-1-carboxylate (Ib).

It has been found that varying the concentration of the compound of formula (I) can modify its effect on the replication of HCV RNA, even to the extent that HCV RNA replication is inhibited. Such compounds may thus have therapeutic applications to treat HCV patients.

Thus, in a further aspect, the present invention provides the use of a compound of formula (I) or a pharmaceutically acceptable salt thereof in the manufacture of a medicament for the treatment of HCV infection.

In a further aspect, the present invention provides a method of treating or preventing a subject suffering from HCV infection by administering an effective amount of a compound of formula (I) or a pharmaceutically acceptable salt thereof.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Suitable salts of the compounds of the present invention include not only the pharmaceutically acceptable salts thereof as hereinbefore described, but also any common salts or quaternary ammonium salts formed, e.g., from inorganic and organic acids. Suitable salts include those derived from inorganic acids such as hydrochloric, hydrobromic, sulfuric, sulfamic, phosphoric, nitric and the like: and the salts prepared from organic acids such as acetic, propionic, succinic, glycolic, stearic, malic, tartaric, citric, ascorbic, mapoic, sulfanilic, 2-acetoxybenzoic, fumaric, toluenesulfonic, methanesulfonic, ethane disulfonic, oxalic, isethionic, trifluoroacetic and the like.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope any enantiomers, diastereomers, geometric isomers and tautomers of the compounds of formula (I). It is to be understood that all such isomers and mixtures thereof are encompassed within the scope of the invention.

In another aspect of the invention, there is provided a method of inhibiting replication of HCV RNA and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I), or a pharmaceutically acceptable salt thereof. "Effective amount" means an amount sufficient to cause a benefit to the subject or at least to cause a change in the subject's condition.

In a further embodiment of the present invention, there is provided the use of a compound of formula (I), or a pharmaceutically acceptable salt thereof, for the manufacture of a medicament for the treatment or prevention of infection by hepatitis C virus, in combination with one or more other agents for the treatment of viral infections such as an antiviral agent, and/or an immunomodulatory agent such as $\alpha$-, $\beta$- or $\gamma$-interferon, particularly $\alpha$-interferon. Suitable antiviral agents include ribavirin and inhibitors of hepatitis C virus (HCV) replicative enzymes, such as inhibitors of metalloprotease (NS2-3), serine protease (NS3), helicase (NS3) and RNA-dependent RNA polymerase (NS5B).

A further aspect of the invention provides a pharmaceutical composition comprising a compound of formula (I) or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

Thus, a further aspect of the invention provides a method of preparation of a pharmaceutical composition by admixing at least one compound of formula (I), or a pharmaceutically acceptable salt thereof, with one or more pharmaceutically acceptable adjuvants, diluents or carriers and/or with one or more other therapeutically or prophylactically active agents.

A further aspect of the invention provides a compound of formula (I) or a pharmaceutically acceptable salt thereof for use in therapy, such as the treatment or prevention of infection by hepatitis C virus.

A further aspect of the invention provides a compound of formula (I) or a pharmaceutically acceptable salt thereof, with the proviso that the compound of formula (I) is not:

tert-butyl 4-(4-{[(4-hydroxyphenyl)amino]carbonyl}phenyl)piperazine-1-carboxylate, tert-butyl 4-(4-{[(4-bromophenyl)amino]carbonyl}phenyl)piperazine-1-carboxylate, tert-butyl 4-(4-{[(3-bromophenyl)amino]carbonyl}phenyl)piperazine-1-carboxylate, tert-butyl 4-{4-[({3-[(1E)-3-methoxy-3-oxoprop-1-en-1-yl]phenyl}amino)carbonyl]phenyl}piperazine-1-carboxylate, tert-butyl 4-{4-[(4-hydroxybenzoyl)amino]phenyl}piperazine-1-carboxylate, or tert-butyl 4-{4-[(4-aminobenzoyl)amino]phenyl}piperazine-1-carboxylate.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. For the treatment or prevention of infection by hepatitis C virus, suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

Compounds of general formula (I) may be prepared by methods disclosed in the documents hereinbefore referred to and by methods known in the art of organic synthesis as set forth below.

Thus, the present invention provides a process for the preparation of a compound of formula (I).

According to a general process (a), compounds of formula (I) may be prepared by the reaction of a compound of formula (II) with a compound of formula (III):

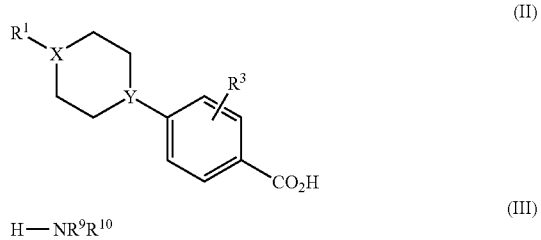

(II)

(III)

H—NR⁹R¹⁰ where $R^1$, $R^3$, X, Y, $R^9$ and $R^{10}$ are as defined for formula (I). The reaction is conveniently performed in the presence of a suitable solvent, such as NMP or DMF, in the presence of a coupling reagent, such as Py-BOP.

Compounds of formula (I) may also be prepared by the reaction of a compound of formula (IV) with a compound of formula (V):

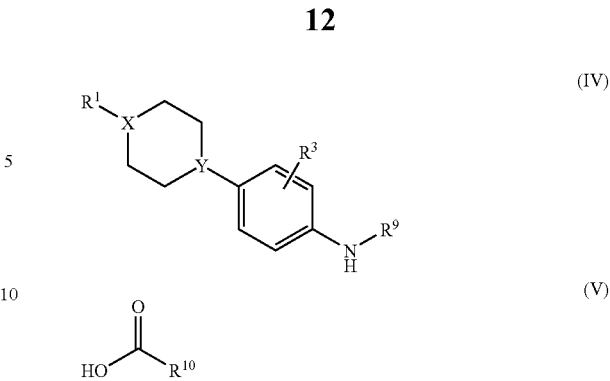

where $R^1$, $R^3$, X, Y, $R^9$ and $R^{10}$ are as defined for formula (I). The reaction is conveniently performed in the presence of a suitable solvent, such as NMP, in the presence of a coupling reagent, such as Py-BOP.

Where they are not commercially available, the starting material of formulae (II), (III), (IV) and (V) may be prepared by methods analogous to those described in the accompanying Schemes and Examples, or by standard methods well known from the art.

General Synthetic Schemes

In general five synthetic schemes were used for the preparation of the compounds.

Method A

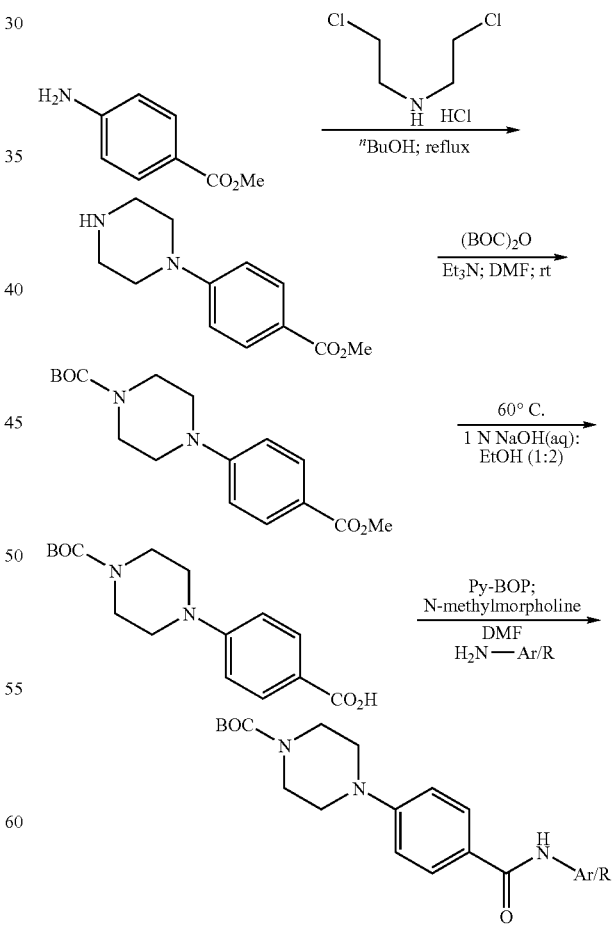

Methyl 4-aminobenzoate was heated at reflux with bis(2-chloroethyl)amine hydrochloride salt in n-butanol for 7 days.

The resultant arylpiperazine product precipitated upon cooling to room temperature and could be readily isolated by filtration. Following capping of the secondary amine with a BOC group, base mediated hydrolysis of the ester functionality afforded the free acid ready for coupling with diverse amines. Amide bond formation was mediated by the peptide coupling reagent Py-BOP in DMF in the presence of organic base. Final products were typically isolated either via direct phase column chromatography or reverse phase HPLC.

Method B

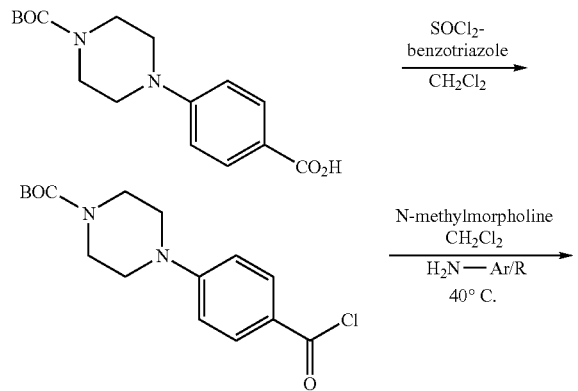

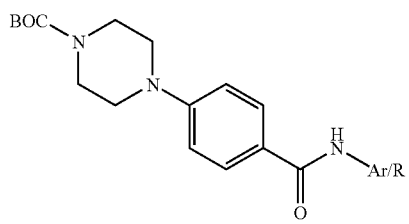

Amide coupling of key carboxylic acid intermediate was effected via formation of the corresponding acid chloride: reaction of the carboxylic acid with a 1:1 stock solution of thionyl chloride:benzotriazole in $CH_2Cl_2$ and filtering off the resultant benzotriazole hydrochloride afforded a stock solution of the acid chloride. Reaction with amines in $CH_2Cl_2$ in the presence of N-methylmorpholine yielded the desired amide. Final products were typically isolated either via direct phase column chromatography or reverse phase HPLC.

Method C

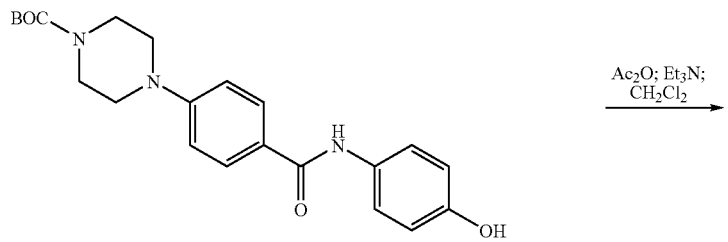

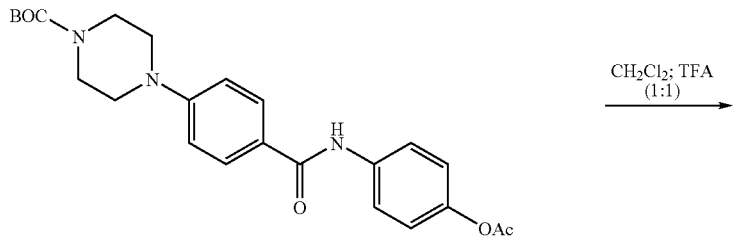

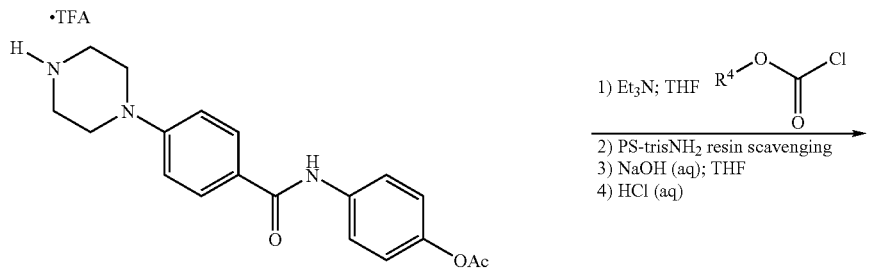

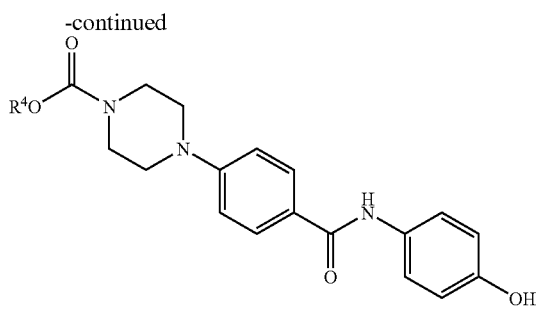

Following protection of the phenolic OH as an acetate ester and removal of the BOC group, urethanes were prepared through reaction of the secondary amine with the appropriate chloroformate in the presence of an organic base. Excess chloroformate reagent was trapped with a scavenger resin, permitting O-acetate protected intermediates to be isolate by simple filtration and evaporation of volatiles. Base mediated hydrolysis of the acetate protecting group followed by acidification yielded the target molecule, which typically could be isolated in sufficient purity either via simple filtration and washing or by reverse phase HPLC.

Method D

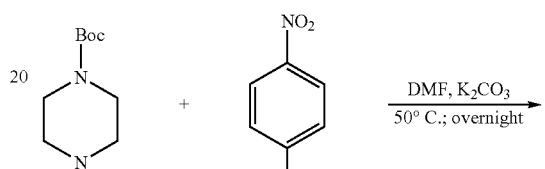

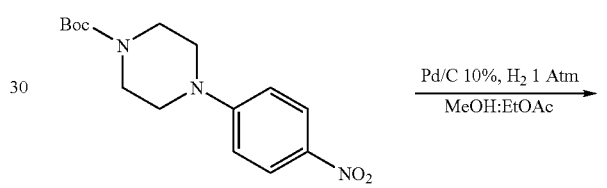

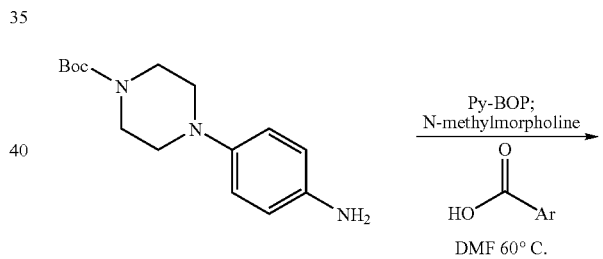

The amide fragment was prepared using methyl 4-bromobenzoate as starting material. At first the methyl ester was hydrolysed with NaOH and the resulting free acid was coupled with 4-aminophenol in DMF, using pyBOP as coupling agent in the presence of N-methylmorpholine. Protection of the hydroxyl group was effected with TBDMSCl in the presence of imidazole. This fragment was then used in the palladium mediated N-arylation of amines. Following work-up and chromatography, the desired O-de-silylated material was isolated directly, without the need for a separate deprotection step.

Method E

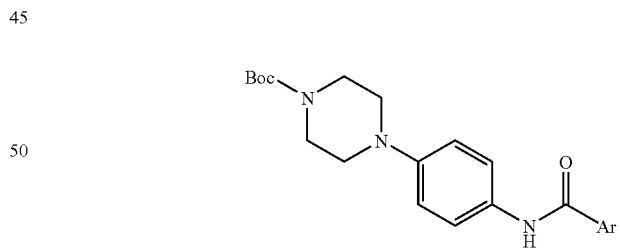

tert-Butyl 4-(4-nitrophenyl)piperazine-1-carboxylate was obtained by nucleophilic aromatic substitution of the fluoro substituent in 4-fluoro-nitrobenzene with tert-butyl-1-piperazine in DMF at 50° C. overnight. Following catalytic hydrogenation to reduce the nitro group and afford the corresponding aniline, the amide bond formation was performed using Py-BOP in DMF in the presence of organic base. The final product was isolated via direct phase column chromatography (60% EtOAc in petroleum ether).

REPRESENTATIVE EXAMPLES
Method A
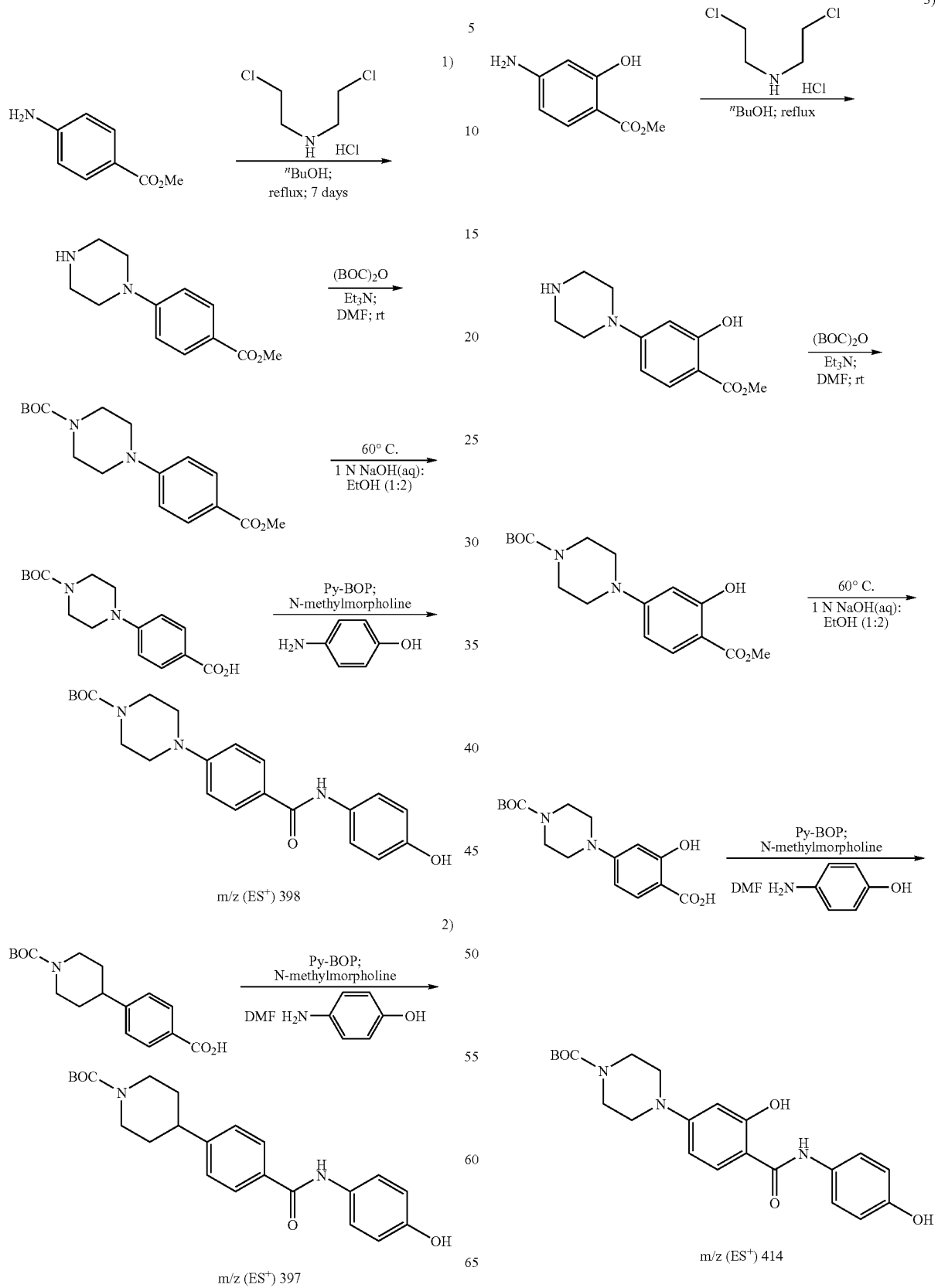

Method B
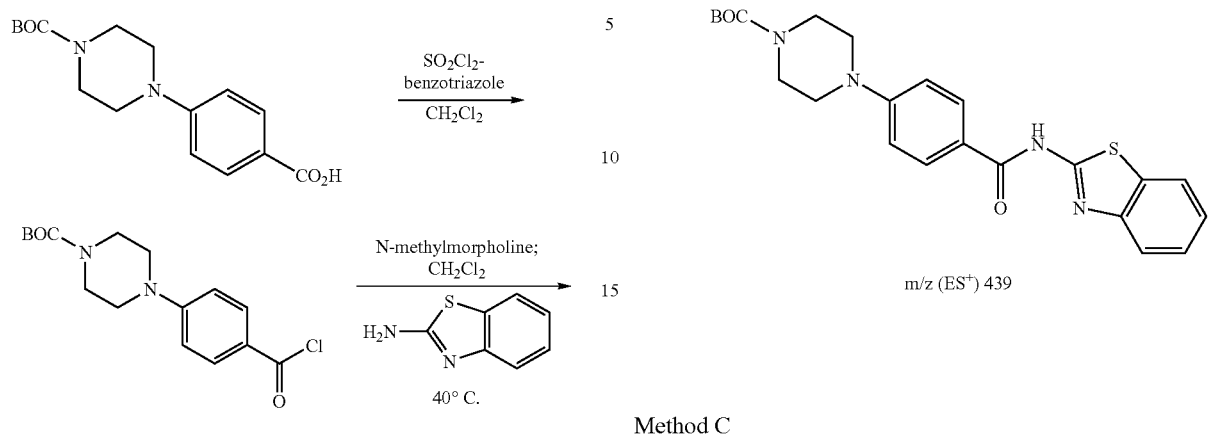
Method C
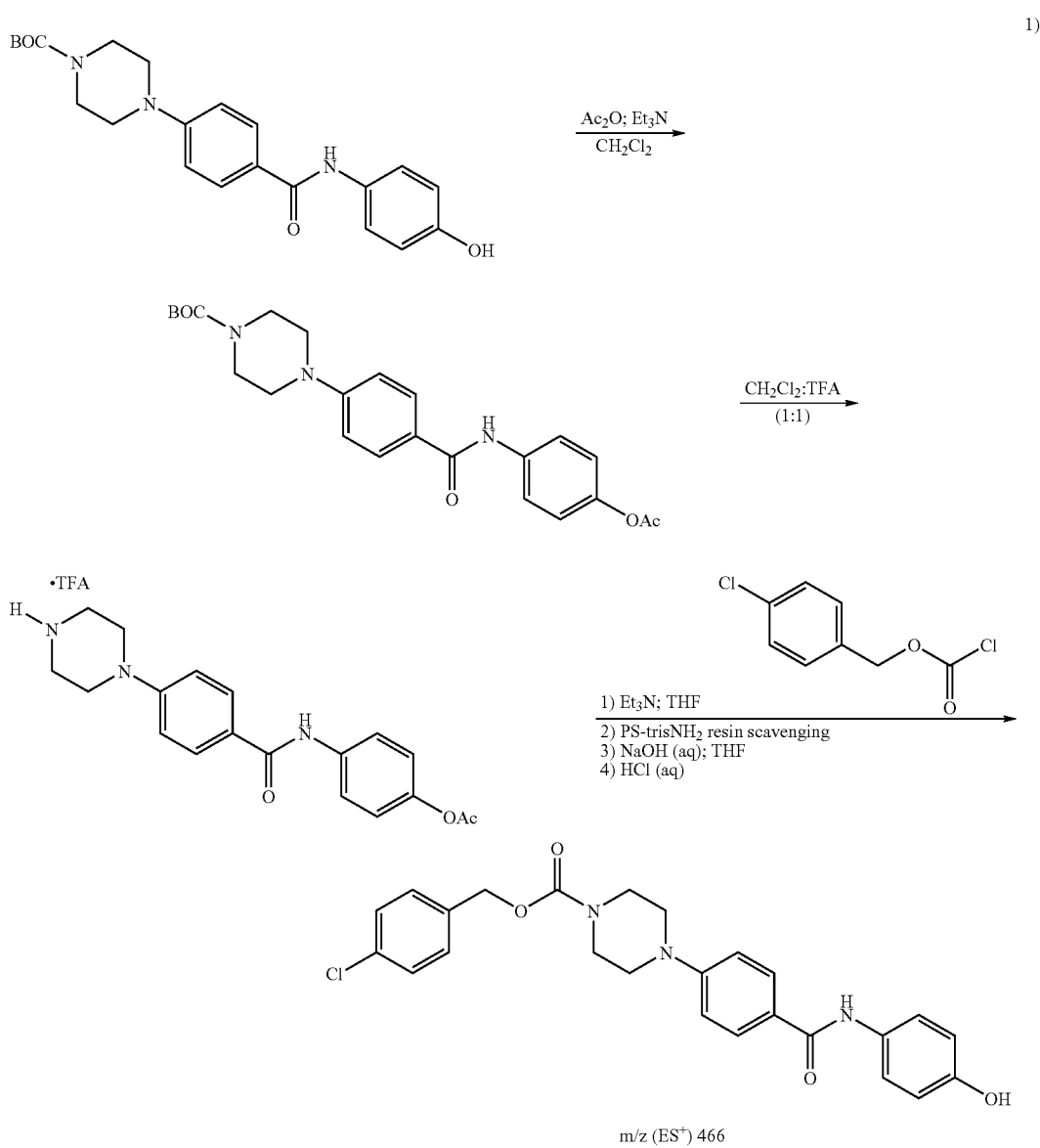

-continued
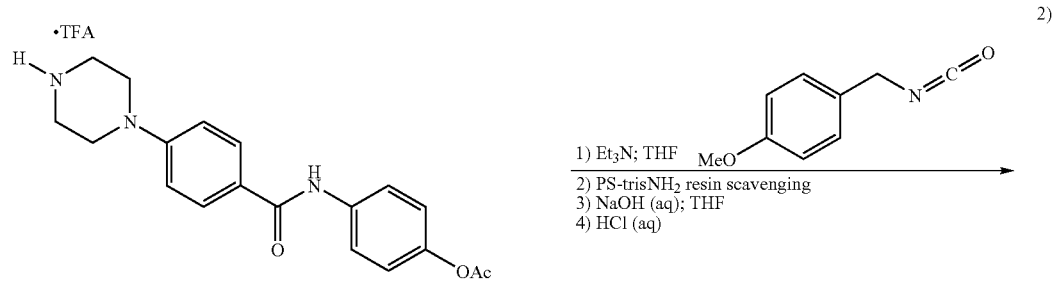
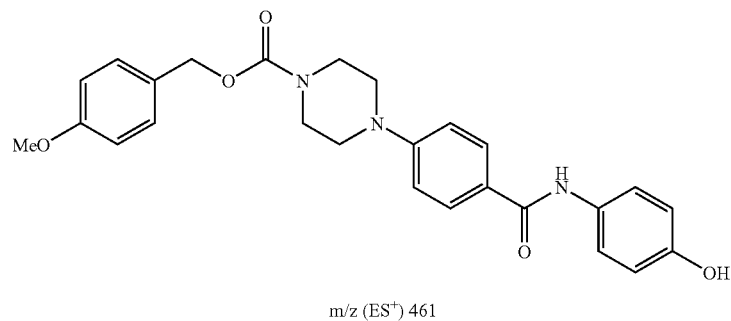
m/z (ES+) 461
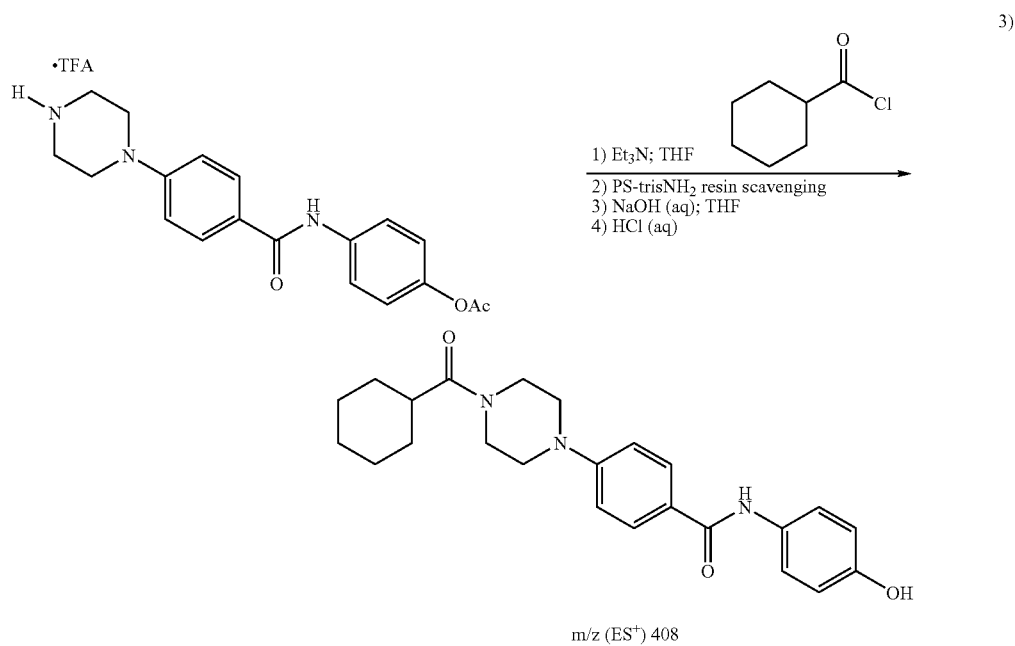
m/z (ES+) 408
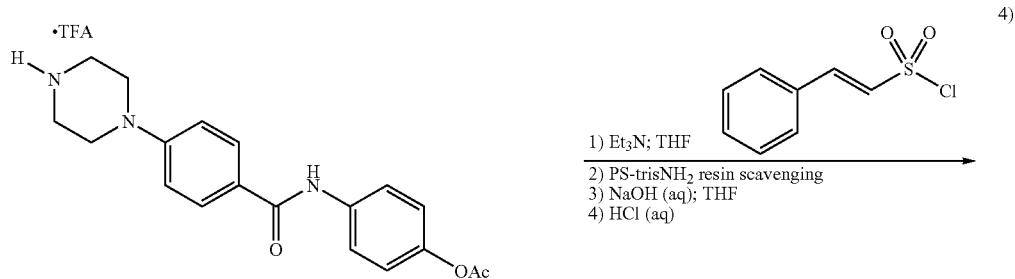

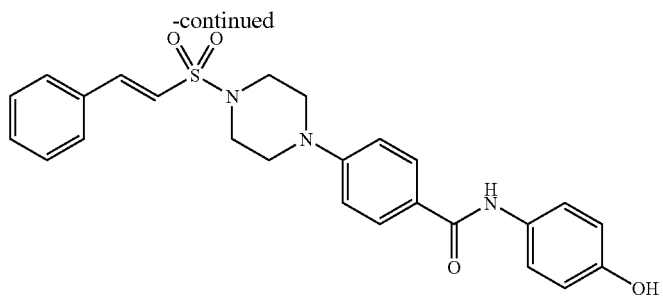

m/z (ES+) 464

Method D

Method E

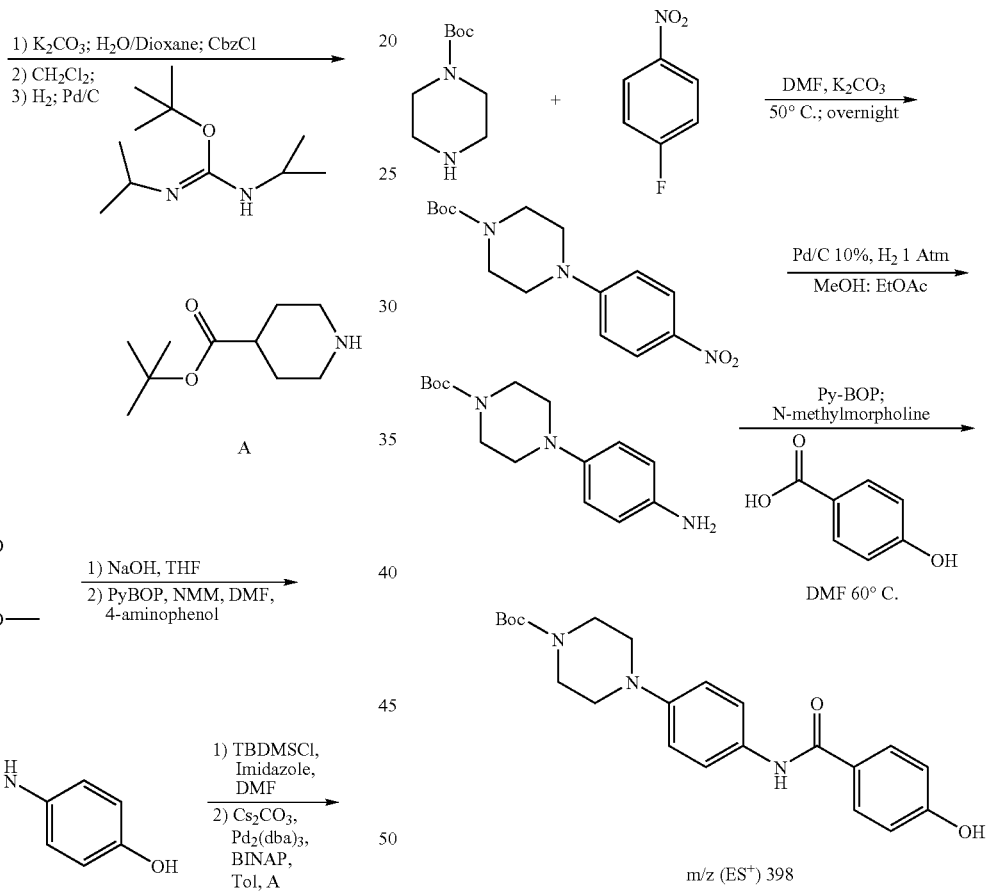

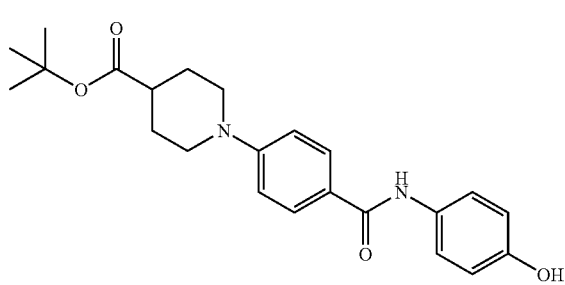

m/z (ES+) 397

It will be understood that any compound of formula (I) initially obtained from any of the above processes may, where appropriate, subsequently be elaborated into a further compound of formula (I) by techniques known from the art.

For instance, a compound of formula (I) where $R^2$ is C(O)NHR$^{10}$, and R$^{10}$ is phenyl substituted with bromine may be transformed into a compound of formula (I) where $R^2$ is C(O)NHR$^{10}$ and R$^{10}$ is phenyl substituted with acrylate by palladium mediated cross-coupling methodology in a suitable solvent, such as acetonitrile, in the presence of phosphine ligands such as P(o-tolyl)$_3$ and an organic base such as triethylamine.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples are illustrative of the invention.

Results

Inhibitory effect of compounds of formula I on HCV replicons. The effect of compounds of formula I on replication of adapted HCV replicons was estimated by using cell lines transiently or stably transfected with HCV replicons. HCV replication and the effect of compounds were measured by using several different methods including Cell-ELISA, beta-lactamase, Northern blot, and in situ RNAse protection assays as described in the methods section. Compounds of formula I had an inhibitory effect on replication of HCV replicons containing adaptive mutations with $IC_{50}$ values in the range from less than 0.1 µM to about 2 µM. As an example, incubation of HBI10A replicon cells with compound (Ib) resulted in a dose-dependent inhibition of HCV replication with an $IC_{50}$ value of 0.12±0.06 µM. Standard MTT cytotoxicity assays and $^{14}C$ thymidine incorporation experiments indicated that compound (Ib) was toxic and inhibited cell proliferation only at concentrations two orders of magnitude higher than those effective on the replicon. The inhibitory effect of compound (Ib) was confirmed also with other cell clones stably expressing different replicons as well as in transient transfection experiments with replicons derived from different HCV isolates and containing different adaptive mutations (Table 7). Interestingly, compound (Ib) inhibited with comparable potency also replication of an adapted full length HCV genome. Moreover, compound (Ib) also inhibited with comparable potencies HCV replicons derived from the Con1 isolate in human HeLa cells and in the mouse hepatoma cell line Hepa1-6, indicating that its effect was independent of the species and the tissue of origin of the host cells.

Stimulatory effect of compounds of formula I. While compounds of formula I inhibited replicons fully competent for replication, they had a stimulatory effect on replicons that replicated inefficiently (Table 8, FIG. 1). This stimulatory effect was studied in detail with compound (Ib). In transient transfection experiments, the pHCVNeo17.wt replicons did not replicate appreciably while the pHCVNeo17.m17 replicon containing the E1202G mutation in NS3 replicated at barely detectable levels. As monitored by the Cell-ELISA assay, the replication of these 2 replicons was stimulated by compound (Ib) in a dose dependent fashion resulting in a bell shaped activation curve (FIG. 1A). The increase in ELISA signal was higher for the pHCVNeo17.m17 replicon than for the pHCVNeo17.wt replicon. However, in both cases the activation peak was observed at compound (Ib) concentrations ranging from about 30 nM to about 120 nM, corresponding approximately to the $IC_{50}$ values measured for highly adapted replicons (Table 7). This activation effect was confirmed also by Northern blot analysis (FIG. 1B). Activation was blocked by IFN, NS3/4A protease and NS5B polymerase inhibitors or genetic inactivation of the NS5B polymerase. Compound (Ib) stimulated replication also of non-adapted full length Con1 genomes, albeit at a lesser extent than that observed with the corresponding replicons. In addition, compound (Ib) also activated replication of non-adapted replicons derived from the BK isolate of HCV. Other compounds of formula I also activated replication of the pHCVNeo17.wt replicon. However, only a subset of the inhibitory compounds showed a measurable activation, suggesting that the two activities could be dissociated (Table 9).

Selection of replicons resistant to compounds of formula I and identification of resistance mutations. In cell-free assays, compounds of formula I do not inhibit the serine protease, ATPase, helicase and polymerase associated with the NS3/4A and NS5B proteins, indicating that their effect on viral replication is not exerted through inhibition of these viral enzymes. In the attempt to identify the molecular target(s) of these compounds, replicons resistant to compound (Ib) were selected by adopting a strategy already used for selecting mutants resistant to NS3-4A protease and NS5B polymerase inhibitors (Trozzi et al., *J Virol* 77, 3669-3679, 2003). Resistant cell clones were phenotypically similar to parental cells, expressed comparable levels of viral RNA and proteins and exhibited reduced susceptibility to compound (Ib) and to other compounds of formula I, with $IC_{50}$ values at least ten times higher than those measured with parental cells (Table 10). These clones were still sensitive to inhibition by interferon-alpha as well as by several inhibitors of the NS5B polymerase and NS3/4A protease, demonstrating that resistance was specific for compounds of formula I (Table 10).

To identify the mutation(s) in the viral genome responsible for the resistance phenotype, replicon cDNAs were rescued from resistant clones 10AB3 and 10AB11 by RT-PCR amplification and sequenced. Besides the adaptive mutations present in the parent clone, resistant replicons contained several different amino acid substitutions in NS5A (Table 11). The role of these mutations was investigated by segregating them in replicon vectors containing none, one or both adaptive mutations present in the parental replicon (E1202G and K@2039) and testing the resulting replicons in transient transfection assays (Table 8). Adapted replicons containing replacement of alanine 92 of NS5A with valine (corresponding to residue 2064 of the HCV polyprotein, and designated A92V or A2064V) or replacement of tyrosine 93 of NS5A with histidine (corresponding to residue 2065 of the HCV polyprotein, and designated Y93H or Y2065H) or replacement of arginine 157 of NS5A with tryptophane (corresponding to residue 2129 of the HCV polyprotein, and designated R2129W or R157W) were clearly resistant to compound (Ib). The $IC_{50}$ values measured for these replicons were similar to those observed in the corresponding resistant clones, indicating that each of these three substitutions could by itself confer resistance to compound (Ib). All other mutations did not apparently affect the sensitivity to inhibition to compound (Ib) indicating that they were probably irrelevant for resistance to this compound. As expected, the adapted replicons carrying the A2064V, Y2065H or R2129W were also resistant to other compounds of formula I, but not to other replication inhibitors, including NS5B polymerase and NS3/4A protease inhibitors. Non adapted replicons carrying the A2064V or Y2065H did not replicate appreciably and were not activated by compounds of formula I, suggesting that inhibition and activation by these compounds were exerted through the same pathway.

Figure 2:
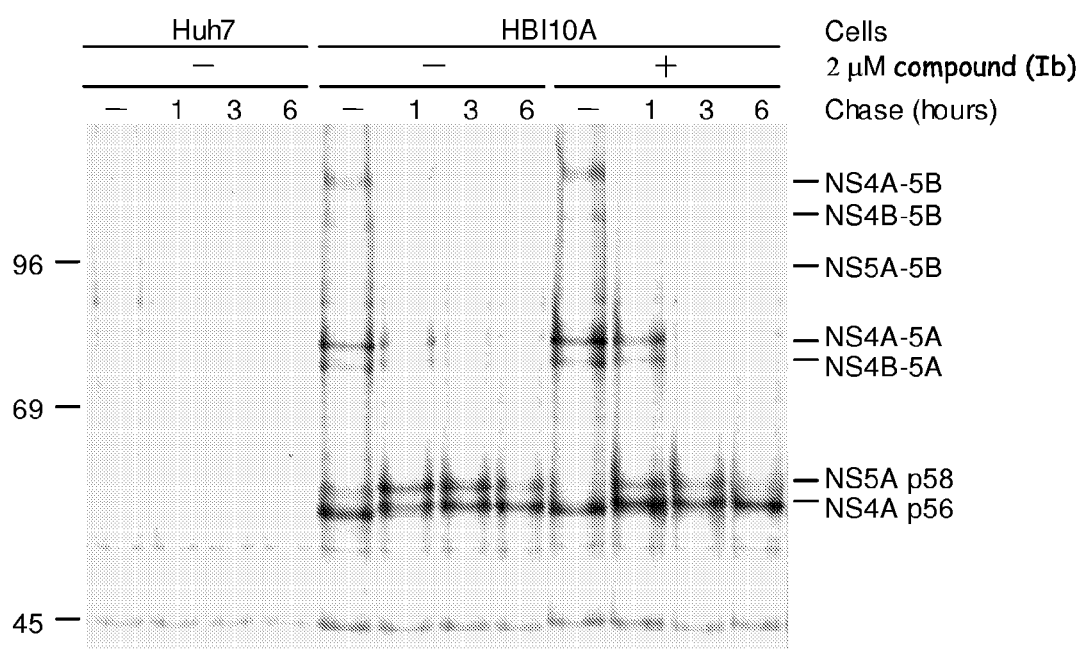
FIG. 2 illustrates effects of an exemplary compound of the invention on biogenesis of the NS5A protein.

Effect of compound (Ib) on biogenesis of the NS5A protein. The localization of resistance mutations in the NS5A protein indicated that both the stimulatory and the inhibitory activity of this compound were exerted by directly or indirectly interfering with the function(s) of the NS5A protein. Therefore, the effect of compound (Ib) on the biogenesis of the NS5A protein was investigated by pulse-chase labeling/immunoprecipitation experiments (FIG. 2). As reported previously, in the absence of inhibitor, mature NS5A protein was released from the viral polyprotein in a time-dependent fashion and appeared first as a 56 kDa form (p56) that was progressively converted to higher molecular mass forms, including the prominent 58 kDa hyperphosphorylated form (p58). In the presence of compound (Ib), the rate and the extent of conversion of the p56 into p58 were reduced, indicating that the compound affected the biogenesis of NS5A possibly by decreasing the extent of hyperphosphorylation.

Materials and Methods

Cells and cell culture. Huh-7 cells were kindly provided by Dr. Ralf Bartenschlager (U. of Heidelberg, Germany). SL1 and MH1 cells were kindly provided from Dr. Christoph Seeger (Fox Chase Cancer Center, Philadelphia, Pa.; USA). HBI10A and other replicon containing cell lines were derived from Huh-7 cells as described in WO2002059321 A2; Mottola et al, *Virology* 293, 31-43, 2002; and Trozzi et al., *J Virol* 77, 3669-3679, 2003. All cells were grown in Dulbecco's modified minimal essential medium (DMEM, Gibco, BRL) supplemented with 10% FCS, except that the medium for HBI10, SL1 and M:H1 cells was supplemented with 0.8 mg/ml G418 (Gibco, BRL). For routine work cells were passed twice a week 1 to 5, using 1× trypsin/EDTA (Gibco, BRL). Preparation of cells cured of endogenous replicons by Interferon treatment (10AIFN), in vitro transcription and RNA transfection, and selection of clones resistant to the test compounds were performed as described by Trozzi et al. J. Virol. 2003, 77:3669-79).

Plasmid construction. cDNA fragments were cloned in the desired expression vectors by standard DNA protocols or by PCR amplification of the area of interest, using synthetic oligonucleotides with the appropriate restriction sites. Plasmid DNA was prepared from overnight culture in Luria Bertani broth using Qiagen columns according to instructions. The sequences of all plasmids were verified by automated sequencing.

Plasmids pHCVNeo17.wt, pHCVNeo17.B (here designated pHCVNeo17.m10), pBK-SI, pBK-RMSI, pFL.wt and pFL.B (here designated pFL.m10) have been already described by Trozzi et al. J. Virol. 2003, 77:3669-79, by Grobler et al J. Biol. Chem. 2003 278(19):116741-46 and by Pacini et al. Anal Biochem. 2004, 331:46-59. All other replicon plasmids designated with the pHCVNeo prefix are identical to plasmid pHCVNeo17.wt but contain the mutations indicated in Table 8. Plasmids designated with the pHCVbla prefix were derived from the corresponding pHCVNeo plasmids by replacing the neomycin phosphotransferase (neo) gene with the β-lactamase (bla) gene as described in WO2003089672 A1 and in Murray et al., J Virol 77, 2928-2935, 2003.

In vitro RNA transcription and RNA transfection were performed as described in WO2002059321 A2; Mottola et al., *Virology* 293, 31-43, 2002; and Trozzi et al., *J Virol* 77, 3669-3679, 2003. Briefly, Plasmids were digested with the ScaI or XbaI endonucleases (New England Biolabs) and transcribed in vitro with the T7 Megascript kit (Ambion). Transcription mixtures were treated with DNase I (0.1 U/ml) for 30 minutes at 37° C. to completely remove template DNA, extracted according to the procedure of Chomczynski (Chomczynski et al., 1987. *Anal. Biochem.* 162, 156-159), and resuspended with RNase-free phosphate buffered saline. RNA transfection was performed by electroporation.

Sequencing of resistant replicons. Total RNA was extracted from selected clones using the Qiagen RNAeasy minikit following manufacturer instructions. Replicon RNAs (2-10 µg of total cellular RNA) were retro-transcribed using oligonucleotide HCVG34 (5'-ACATGATCTGCA-GAGAGGCCAGT-3') and the Superscript II reverse transcriptase (Gibco, BRL) according to manufacturer instructions, and subsequently digested with 2 U/ml Ribonuclease H (Gibco BRL). The cDNA regions spanning from the EMCV IRES to the HCV 3' end were amplified by PCR using oligonucleotides HCVG39 (5'-GACASGCTGT-GATAWATGTCTCCCCC-3') and CITE3 (5'-TG-GCTCTCCTCAAGCGTATTC-3') and the LA Taq DNA polymerase (Takara). Amplified cDNAs were either sequenced directly or digested with the appropriate restriction endonucleases (New England Biolabs) and cloned into plasmids pHCVNeo17.wt, pHCVNeo17.m5 or pHCVNeo17.m10 digested with the same endonucleases. The presence of the desired DNA insert was ascertained by restriction digestion, and the nucleotide sequence of NS region of each plasmid was determined by automated sequencing. Nucleotide sequences and deduced amino acids sequences were aligned using the Vector NTI software.

Metabolic labeling and immunoprecipitation.

Huh-7 and HBI10A cells were seeded in 6-well plates at a density of $4\times10^5$ cells/well. For pulse-chase metabolic labeling with $^{35}S$ amino acids, cells were incubated in methionine/cysteine-free DMEM supplemented with 1% dialyzed FCS for 1 h, labeled for 30' with the same medium containing 200 µCi/ml of ($^{35}S$) protein labeling mix (Du-Pont NEN) and then either lysed or chased for various times (1-3-6 hours) in complete medium supplemented with a 10-fold excess of methionine/cysteine. Cells were lysed in 0.2 ml of TNE lysis buffer (20 mM Tris-HCl, pH 7.5, 150 mM NaCl, 1 mM EDTA, 1% SDS) containing Complete protease inhibitor (Boehringer). Supernatants and cell lysates were centrifuged for 15 min at 14,000 rpm at 4° C. to remove nuclei and debris. Immunoprecipitation and analysis on SDS-PAGE was performed as described by Trozzi et al. J. Virol. 2003, 77:3669-79). Gels were exposed to X-ray film or to phosphorimaging screen for quantitative analysis with the Molecular Dynamics system.

Northern blot hybridization The effect of the test compounds on viral replication and the replication proficiency of the mutant replicons was estimated by monitoring expression of HCV replicon RNA by Northern blot hybridization as described by Trozzi et al. J. Virol. 2003, 77:3669-79.

Cell ELISA assays. The effect of the test compounds on viral replication and the replication proficiency of the mutant replicons was estimated by monitoring expression of the NS3 protein by Cell-ELISA with the anti-NS3 mab 10E5/24 as described by Trozzi et al. J. Virol. 2003, 77:3669-79). Compounds were dissolved and serially diluted in dimethyl sulfoxide (DMSO) in such a way that the final DMSO concentration was 1%. Transient transfection assays were performed with 10AIFN cells, prepared and transfected by electroporation as described by Trozzi et al. J. Virol. 2003, 77:3669-79). Cells were supplemented with the compounds between 1 and 4 hours after transfection.

Beta-lactamase gene reporter assay (BLA-assay). The effect of the test compounds on viral replication and the replication proficiency of the mutant replicons was estimated by monitoring expression the Beta-lactamase enzyme according to Murray et al., *J Virol* 77, 2928-35, 2003. Beta-lactamase activity was measured with a fluorescence plate reader that quantitates the amount of green (530 nm) or blue (460 nm) fluorescence emitted by cells stimulated with light of 405 nm.

Figure Legends

FIG. 1 Effect of compound (Ib) on replication of wt and adapted replicons. 10AIFN cells were transfected with wild type pHCVNeo17.wt replicon (grey), the fully adapted pHCVNeo17.m10 replicon carrying the E1202G and the K@2039 mutations (white), the partially adapted pHCVNeo17.m17 replicon carrying only the E1202G mutation (black), or the compound (Ib) resistant pHCVNeo17.m29 replicon carrying the E1202G, K@2039 and A2064V mutations. Transfected cells were cultured in absence or in the presence of the indicated concentrations of compound (Ib). HCV replication was monitored by Cell-ELISA (A) or Northern Blot (B) as indicated in the methods section.

FIG. 2 Effect of compound (Ib) on the biogenesis of the NS5A protein. Huh-7 (lanes 1 to 4) and HBI10A (lanes 5 to 12) were pulse-labeled with $^{35}$S amino acids for 20' at 37° C. and then chased for the time (in hours) indicated above each lane. Where indicated starvation, labeling and chase were performed in the presence of 2 µM compound (Ib). Labeled proteins were immunoprecipitated with the 551V anti-NS5A antiserum and analyzed by SDS-10% PAGE. Positions of molecular mass standards (in kilodalton), NS5A forms and uncleaved precursors are indicated.

TABLE 7

Inhibitory effect of compound (Ib) on subgenomic and genomic HCV replicons derived from different viral isolates and containing different combinations of adaptive mutations. Mutated residues are indicated according to their position in the full length polyprotein encoded by the Con1 HCV genome (EMBL-Genbank no. AJ238799). The indicated replicons were transfected in 10AIFN cells and the effect of compound (Ib) was monitored by Cell-ELISA four days after transfection.

| replicon | | Subgenomic | | | | Genomic |
|---|---|---|---|---|---|---|
| | | pHCVNeo17.m10 | pHCVNeo17.SI | pHCVNeo17.RG | pBK-RMSI | pFL.m10 |
| HCV isolate | | Con1 | Con1 | Con1 | BK | Con1 |
| Adaptive | NS3 | E1202G | | | R1496M | E1202G |
| Mutations | NS5A | K@2039 | S2204I | | S2204I | K@2039 |
| | NS5B | | | R2884G | | |
| IC$_{50}$ (µM) | | 0.1 | 0.1 | <0.05 | 0.65 | 0.07 |

TABLE 8

Replication competence and sensitivity to compound (Ib) of mutant replicons. Nucleotide substitutions (italic) and resulting amino acid mutations (bold) present in each replicon are indicated according to their positions in the RNA sequence of the HCV isolate Con1 (EMBL-Genbank no. AJ238799) and in the corresponding polyprotein. HCV replication and the effect of the compounds were monitored by Cell-ELISA.

| Replicon pHCV Neo17. | Mutations | | | | | Replication efficiency NU$^a$ | Cmpd Ib IC$_{50}$ (µM) |
|---|---|---|---|---|---|---|---|
| | NS3 | | NS5A | | | | |
| Wt | | | | | | 0.9 | $^b$activation |
| m5 | | K@2039 *AAA6458* | | | | 3.0 | 0.1 |
| m10 | E1202G *A3946C* | K@2039 *AAA6458* | | | | 15.5 | 0.1 |
| m17 | E1202G *A3946C* | | | | | 1.5 | activation |
| m30 | | H2057R *A6511G* | | | | 2 | activation |
| m31 | | | A2064V *C6532T* | | | 0.9 | No effect |
| m35 | | | Y2065H *T6532C* | | | 0.9 | No effect |
| m33 | | K@2039 *AAA6458* | H2057R *A6511G* | | | 20 | 0.031 |
| m32 | | K@2039 *AAA6458* | A2064V *C6532T* | | | 2.8 | >2 |
| m36 | | K@2039 *AAA6458* | Y2065H *T6532C* | | | 5 | >2 |
| m50 | | K@2039 *AAA6458* | | R2129W *C6726T* | | 4.7 | >2 |
| m21 | | K@2039 *AAA6458* | | | S2404P *T7551C* | 4.5 | 0.038 |
| m29 | | K@2039 *AAA6458* | H2057R *A6511G* | A2064V *C6532T* | | 18 | >2 |

TABLE 8-continued

Replication competence and sensitivity to compound (Ib) of mutant replicons. Nucleotide substitutions (italic) and resulting amino acid mutations (bold) present in each replicon are indicated according to their positions in the RNA sequence of the HCV isolate Con1 (EMBL-Genbank no. AJ238799) and in the corresponding polyprotein. HCV replication and the effect of the compounds were monitored by Cell-ELISA.

| Replicon pHCV Neo17. | Mutations NS3 | | | | NS5A | | | | Replication efficiency NU[a] | Cmpd Ib IC$_{50}$ (µM) |
|---|---|---|---|---|---|---|---|---|---|---|
| m47 | E1202G *A3946C* | K@2039 *AAA6458* | H2057R *A6511G* | | | | | | 17 | 0.06 |
| m44 | E1202G *A3946C* | K@2039 *AAA6458* | | A2064V *C6532T* | | | | | 15 | >2 |
| m65 | E1202G *A3946C* | K@2039 *AAA6458* | | | R2129W *C6726T* | | | | 5 | >2 |
| m52 | E1202G *A3946C* | K@2039 *AAA6458* | | | | T2216I *C6988T* | | | 18 | 0.04 |
| m22 | E1202G *A3946C* | K@2039 *AAA6458* | | | | | S2404P *T7551C* | | 17 | 0.038 |
| m91 | E1202G *A3946C* | K@2039 *AAA6458* | | | | | | D2415G *A7585G* | ? | ? |
| m46 | E1202G *A3946C* | K@2039 *AAA6458* | H2057R *A6511G* | A2064V *C6532T* | | | | | 20 | >2 |
| m43 | E1202G *A3946C* | | | A2064V *C6532T* | | | | | 1 | No effect |
| m45 | E1202G *A3946C* | | H2057R *A6511G* | | | | | | 1 | activation |
| m48 | E1202G *A3946C* | | H2057R *A6511G* | A2064V *C6532T* | | | | | 1.2 | No effect |

[a] replication efficiency is expressed in normalised units (NU)
[b] activation: compound (Ib) activated replication of these mutant replicons.

TABLE 9

Comparison of the activation and inhibition properties of a selected group of compounds of formula I. 10AIFN cells were transfected with pHCVNeo17.wt replicon (Activation) or with the pHCVNeo17.m10 replicon (Inhibition) and cultured for 4 days in the presence of different concentrations of the indicated compounds. HCV replication and the effect of the compounds were monitored by Cell-ELISA. Activity ranges were classified in two groups: A (most active) < 1 µM; B (least active) > 1 µM.

| Compound Example number | Replicon Inhibition Range IC$_{50}$ | Replicon Activation Yes/No |
|---|---|---|
| 101 | A | Yes |
| 303 | A | Yes |
| 123 | A | Yes |
| 302 | A | Yes |
| 216 | A | Yes |
| 116 | A | No |
| 403 | A | No |
| 103 | A | No |
| 306 | A | No |
| 112 | A | No |
| 401 | A | No |
| 603 | B | No |
| 108 | B | No |
| 201 | B | No |
| 503 | B | No |
| 602 | B | No |
| 115 | B | No |

TABLE 10

Effect of replication inhibitors on parental (HBI10A) and compound (Ib) resistant clones (10AB2, 10AB3, 10AB7, and 10AB11). The effect of the interferon (IFN) and of compound (Ib) was monitored by Cell-ELISA.

| | IC$_{50}$ | |
|---|---|---|
| Clone | Compound (Ib) (µM) | IFN (IU/ml) |
| HBI10A | 0.1 ± 0.05 | 2.04 |
| 10AB2 | >2 | NT |
| 10AB3 | >2 | 0.74 |
| 10AB7 | >2 | NT |
| 10AB11 | >2 | 2.16 |

NT, not tested

TABLE 11

Sequence analysis of replicons derived from clones 10AB3 and 10AB11 resistant to compound (Ib). Mutated residues are indicated according to their position in the full length polyprotein encoded by the Con1 HCV genome (EMBL-Genbank no. AJ238799).

| Clone | isolate | NS5A mutations | | | | |
|---|---|---|---|---|---|---|
| 10AB11 | A | K@2039 | R2129W | T2216I | D2415G | |
| 10AB3 | B | K@2039 | H2057R | A2064V | A2367V | S2404P |
| 10AB3 | C | K@2039 | Y2065H | P2161T | K2187N | S2404P |

General Procedures

All solvents were obtained from commercial sources (Fluka, puriss.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al., J. Org. Chem. 1978, 43, 2923) or on commercial flash chromatography systems (Biotage corporation and Jones Flashmaster II) utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H NMR spectra were recorded on Bruker AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; br, broad, and combinations thereof); coupling constant(s) in hertz (Hz); number of protons. Mass spectral (MS) data were obtained on a Perkin Elmer API 100, or Waters MicroMass ZQ, operating in negative (ES$^-$) or positive (ES$^+$) ionization mode and results are reported as the ratio of mass over charge (m/z) for the parent ion only. Preparative scale HPLC separations were carried out on a Waters Delta Prep 4000 separation module, equipped with a Waters 486 absorption detector or on a Gilson preparative system. In all cases compounds were eluted with linear gradients of water and acetonitrile both containing 0.1% TFA using flow rates between 15 and 25 mL/min.

The following abbreviations are used in the examples, the schemes and the tables: Ac$_2$O: acetic anhydride; BINAP: (+/−)-1,1'-bi-2-naphthol; (BOC)$_2$O: di-tert-butyl dicarbonate; BuOH: n-butanol; CbzCl: benzyl chloroformate; CDCl$_3$: chloroform-D; DCM: dichloromethane; DIEA: diisopropylethyl amine; DME: dimethoxyethane; DMF: dimethylformamide; DMSO: dimethylsulfoxide; eq.: equivalent(s); Et$_3$N: triethylamine; EtOAc: ethyl acetate; Et$_2$O: diethyl ether; EtOH: ethanol; h: hour(s); HATU: O-(7-azabenzotriazol-1-yl)-N,N,N',N'-tetramethyluronium hexafluorophophate; Me: methyl; MeCN: acetonitrile; MeOH: methanol; min: minutes; NBS: N-bromo succinimide; NMM: N-methyl morpholine; Pd$_2$(dba)$_3$: tris(dibenzylideneacetone)dipalladium(0); PE: petroleum ether; Ph: phenyl; PS: polystyrene; PyBop: (1H-1,2,3-benzotriazol-1-yloxy)(tripyrrolidin-1-yl)phosphonium hexafluorophosphate; RP-HPLC: reversed phase high-pressure liquid chromatography; RT: room temperature; TBDMSCl: tert-butyldimethylsilyl chloride; TFA: trifluoroacetic acid; THF: tetrahydrofuran; TLC: thin layer chromatography; TMS: trimethylsilyl; Tol: toluene.

General Procedure for Preparation of tert-butyl 4-[4-(aryl/alkylaminocarbonyl)phenyl]piperazine-1-carboxylate:

Step 1: tert-butyl 4-[4-(chlorocarbonyl)phenyl]piperazine-1-carboxylate

A stock solution of SOCl$_2$-benzotriazole in dry DCM (1.5 M) was prepared by making up volume of a viscous clear solution of thionyl chloride (1 eq) and benzotriazole (1 eq) with dry DCM (1.5 M)—cf, Synlett 1999, 1763. 1.25 eq of this stock solution was added to a solution of 4-(4-tert-butoxycarbonyl)piperazin-1-yl)benzoic acid (1 eq) (prepared as described in published International patent application WO98/00134) in dry DCM (0.05 M). With the addition, a precipitate formed that was indicative of acyl chloride formation. The reaction was left at RT for 10 min before being filtered through a pad of anhydrous sodium sulfate.

Step 2: tert-butyl 4-[4-(aryl/alkylaminocarbonyl) phenyl]piperazine-1-carboxylate formation To a solution of aryl- or alkylamine to be used in the coupling (1 eq) in dry DCM (0.3 M) and N-methylmorpholine (2.5 eq), a solution of the acyl chloride (from step 1 above) (1 eq) in DCM (0.05 M) was added. The reaction was heated to 40° C. with stirring overnight. The resulting mixture was allowed to cool to RT, diluted with EtOAc and washed with aqueous HCl (1 N), saturated aqueous Na$_2$CO$_3$ and brine. The organics were then dried over Na$_2$SO$_4$, filtered and evaporated in vacuo. Purification was by automated RP-LCMS. Conditions: X-Terra (Waters) C18 column 5 μm, 19×100 mm; flow: 20 ml/min; Gradient: A H$_2$O+0.1% TFA; B: MeCN+0.1% TFA. Fractions containing pure product were pooled and lyophilized to give the title compounds (20%-68%).

Example 1 tert-butyl 4-(4-{[(4-cyanophenyl)amino] carbonyl}phenyl)piperazine-1-carboxylate $^1$H NMR (400 MHz, DMSO-d$_6$, 300 K) δ 1.42 (s, 9H), 3.29-3.32 (m, 4H), 3.45-3.48 (m, 4H), 7.03 (d, J 8.8, 2H), 7.78 (d, J 8.8, 2H), 7.89 (d, J 8.8, 2H), 7.98 (d, J 8.8, 2H), 10.32 (s, 1H); MS (ES$^+$) m/z 407 (M+H)$^+$ Example 2 tert-butyl 4-{4-[(1,3-benzothiazol-2-ylamino)carbonyl]phenyl}piperazine-1-carboxylate $^1$H NMR (400 MHz, DMSO-d$_6$, 300 K) δ 1.43 (s, 9H), 3.35-3.37 (m, 4H), 3.45-3.47 (m, 4H), 7.03 (d, J 8.8, 2H), 7.31 (m, 1H), 7.45 (m, 1H), 7.75 (d, J 8.0, 1H), 7.99 (d, J 8.0, 1H), 8.06 (d, J 8.8, 2H), 12.53 (s, 1H); MS (ES$^+$) m/z 439 (M+H)$^+$ Example 3 isobutyl 4-(4-{[(4-hydroxyphenyl)amino] carbonyl}phenyl)piperazine-1-carboxylate Step 1: tert-butyl 4-[4-(1-{[4-(acetyloxy)phenyl] amino}vinyl)phenyl]piperazine-1-carboxylate 1.1 eq of Et$_3$N and 2 eq of Ac$_2$O were added to a solution of tert-butyl 4-(4-{[(4-hydroxyphenyl)amino] carbonyl}phenyl)piperazine-1-carboxylate in dry DCM (0.1 M) (prepared as described in published International patent application WO98/00134) and the solution stirred at RT for 16 h under a nitrogen atmosphere. The reaction mixture was diluted with DCM and the organic phase was washed with aqueous HCl (1N) (twice), saturated aqueous NaHCO$_3$ and then brine. The organic phase was dried over Na$_2$SO$_4$, filtered and the solvent evaporated in vacuo to afford the title compound as a white solid (90%); MS (ES$^+$) m/z 440 (M+H)$^+$ Step 2: 4-[4-({[4-(acetyloxy)phenyl] amino}carbonyl)phenyl]piperazin-1-ium trifluoroacetate tert-butyl 4-[4-(1-{[4-(acetyloxy)phenyl]amino}vinyl) phenyl]piperazine-1-carboxylate (0.1 M) in a solution of DCM/TFA (2/3) was stirred at RT for 30 min. The organic solvent was evaporated in vacuo and the crude residue was scratched with Et$_2$O. The resultant white solid precipitate was filtered off to afford the title compound (95%); MS (ES$^+$) m/z 339 (M+H)$^+$ Step 3: isobutyl 4-(4-{[(4-hydroxyphenyl)amino]carbonyl}phenyl)piperazine-1-carboxylate 2 eq of isobutyl-chloroformate and 3.5 eq of Et$_3$N were added to a solution of 4-[4-({[4-(acetyloxy)phenyl]amino}carbonyl)phenyl]piperazin-1-ium trifluoroacetate in dry THF (0.05 M) and the solution was allowed to stir at RT for 3 h under N$_2$. PS-trisamine resin (excess) was added and the reaction mixture was stirred for 16 h. The resin and a white precipitate were filtered off. Excess aqueous NaOH (1 M) was added to the organic solution and the reaction mixture was stirred for 2 h. The organic solvent was removed in vacuo and aqueous HCl (1 M) was added until precipitation of a white solid that was filtered off, washed and dried in vacuo to afford the title compound (90%).

$^1$H NMR (300 MHz, DMSO-d$_6$, 300 K) δ0.89 (d, J 6.6, 6H), 1.80-1.93 (m, 1H), 3.20-3.39 (m, 4H, obscured by water peak), 3.4-3.6 (m, 4H), 3.81 (d, J 6.3, 2H), 6.70 (d, J 9.0, 2H), 7.00 (d, J 9.0, 2H), 7.48 (d, J 8.7, 2H), 7.84 (d, J 8.7, 2H), 9.15 (s, 1H), 9.70 (s, 1H); MS (ES$^+$) m/z 398 (M+H)$^+$ Example 4 tert-butyl 1-(4-{[(4-hydroxyphenyl)amino]carbonyl}phenyl)piperidine-4-carboxylate Step 1: 4-bromobenzoic acid 1.1 eq of aqueous NaOH (1 M solution) was added to a solution of methyl 4-bromobenzoate in THF (0.5 M) and the reaction allowed to stir at RT overnight. THF was removed in vacuo and aqueous HCl (6M) was added dropwise to the basic solution at 0° C. to adjust the pH to pH 2. The resultant aqueous mixture was extracted with EtOAc (3×) and then the combined organics were washed with brine, dried over Na$_2$SO$_4$, filtered and the solvent evaporated in vacuo. The title compound was obtained in quantitative yield; MS (ES$^+$) m/z 201 (M+H)$^+$, m/z 203 (M+H)+

Step 2: 4-bromo-N-(4-hydroxyphenyl)benzamide

To a solution of 4-bromobenzoic acid in DMF (0.10 M), 3 eq of NMM, 1.5 eq of Py-BOP and 1.1 eq of 4-aminophenol were added and the mixture was stirred at RT for 20 min. DMF was concentrated in vacuo and the residue diluted with EtOAc and aqueous HCl (1N). The resultant precipitate was filtered off and dried in vacuo to afford the title compound (73%); MS (ES$^+$) m/z 292 (M+H)$^+$, m/z 294 (M+H)$^+$ Step 3: 4-bromo-N-(4-{[tert-butyl(dimethyl)silyl]oxy}phenyl)benzamide To a solution of 4-bromo-N-(4-hydroxyphenyl)benzamide in DMF (1.3 M), 2.5 eq of imidazole and 1.2 eq of TBDMSCl were added and the solution stirred at RT for 30 minutes. The reaction mixture was diluted with EtOAc. The organic phase was washed with aqueous HCl (1N), saturated aqueous NaHCO$_3$ and brine. The organic phase was dried over Na$_2$SO$_4$, filtered and concentrated in vacuo to afford the title compound (95%); MS (ES$^+$) m/z 406 (M+H)$^+$, m/z 408 (M+H)$^+$ Step 4: 1-[(benzyloxy)carbonyl]piperidine-4-carboxylic acid To a solution of piperidine-4-carboxylic acid in a 1:1 mixture of H$_2$O/dioxane (0.4 M), 5 eq of K$_2$CO$_3$ were added before dropwise introduction at 0° C. of 1.1 eq of benzyl chloroformate. The reaction was stirred at RT overnight. The reaction was first washed with Et$_2$O. The aqueous phase was acidified to pH 2 with aqueous HCl (6N) before being extracted with EtOAc (3×). The combined organics were washed with brine, dried over Na$_2$SO$_4$, filtered and concentrated in vacuo to give the product (91%); MS (ES$^+$) m/z 264 (M+H)$^+$ Step 5: 1-benzyl 4-tert-butyl piperidine-1,4-dicarboxylate To a solution of 1-[(benzyloxy)carbonyl]piperidine-4-carboxylic acid in DCM (0.2 M), 3 eq of tert-butyl. N,N'-diisopropylimidocarbamate were added and the mixture was stirred at RT. After 30 min, a further 1.5 eq of tert-butyl N,N'-diisopropylimidocarbamate were added and the solution stirred for an additional hour. The solution was filtered through a pad of celite and then through a pad of silica gel to give the product (83%); MS (ES$^+$) m/z 320 (M+H)$^+$ Step 6: tert-butyl piperidine-4-carboxylate To a solution of 1-benzyl 4-tert-butyl piperidine-1,4-dicarboxylate in EtOAc (0.1 M), a catalytic amount of Pd/C (5%) was added and the atmosphere in the reaction vessel charged with H$_2$ (1 atmosphere). The reaction mixture was stirred vigorously at RT for 8 h. The solution was filtered and the filtrate concentrated in vacuo to afford the title compound (76%); MS (ES$^+$) m/z 186(M+H)$^+$ Step 7: tert-butyl 1-(4-{[(4-hydroxyphenyl)amino]carbonyl}phenyl)piperidine-4-carboxylate An oven dried flask was charged with 1.4 eq of Cs$_2$CO$_3$, then 0.01 eq of Pd$_2$(dba)$_3$ and 0.015 eq of BINAP were added followed by 1 eq of 4-bromo-N-(4-{[tert-butyl(dimethyl)silyl]oxy}phenyl)benzamide and 1.2 eq of tert-butyl piperidine-4-carboxylate. To this mixture, toluene was added to give a 0.16 M solution of 4-bromo-N-(4-{[tert-butyl(dimethyl)silyl]oxy}phenyl)benzamide. The atmosphere in the flask was evacuated and backfilled with Argon before heating the solution at reflux overnight. The reaction mixture was concentrated in vacuo and the crude purified directly by flash chromatography on silica gel (EtOAc:PE=3:7) to afford the title compound (33%).

$^1$H NMR (300 MHz, DMSO-d$_6$, 300 K) δ1.43 (s, 9H), 1.60-1.67 (m, 2H), 1.85-1.93 (m, 2H), 2.41-2.49 (m, 1H), 2.88-3.15 (m, 2H), 3.75-3.82 (m, 2H), 6.72 (d, J 9.0, 2H), 6.97 (d, J 9.0, 2H), 7.50 (d, J 8.6, 2H), 7.84 (d, J 8.6, 2H), 8.99 (s, 1H), 9.57 (s, 1H); MS (ES$^+$) m/z 397 (M+H)$^+$

Example 5 tert-butyl 4-{4-[(4-hydroxybenzoyl)amino]phenyl}piperazine-1-carboxylate

Step 1: tert-butyl 4-(4-nitrophenyl)piperazine-1-carboxylate

To a solution of tert-butyl-piperazine (1 eq) and 4-fluoronitrobenzene (1.1 eq) in DMF (0.43 M), K$_2$CO$_3$ (1.1 eq) was added. The mixture was heated to 50° C. with stirring overnight. At this time the reaction was allowed to cool to RT and partitioned between EtOAc and 1N aqueous HCl. The aqueous fraction was extracted with EtOAc and the combined organics washed with brine, before being dried over $Na_2SO_4$, filtered and evaporated in vacuo to afford the title compound as yellow solid (97%); MS ($ES^+$) m/z 308 $(M+H)^+$.

Step 2: tert-butyl 4-(4-aminophenyl)piperazine-1-carboxylate

Pd on C 10% (0.3% p/p) was added to a solution of tert-butyl 4-(4-nitrophenyl)piperazine-1-carboxylate (1 eq) in a mixture (1:1 ratio) MeOH:EtOAc (0.03 M). The atmosphere in the reaction vessel was charged with $H_2$ (1 atm.) and the reaction stirred vigorously for 2 h. At this time, the reaction mixture was filtered through a pad of celite and concentrated in vacuo to afford the title compound (quant); MS ($ES^+$) m/z 278 $(M+H)^+$ Step 3: tert-butyl 4-{4-[(4-hydroxybenzoyl)amino]phenyl}piperazine-1-carboxylate To a solution of tert-butyl 4-(4-aminophenyl)piperazine-1-carboxylate (1 eq), 4-hydroxybenzoic acid (1.1 eq), N-methylmorpholine (3 eq) in dry DMF (0.16 M), was added PyBop (1.5 eq). The reaction mixture was heated at 60° C. with stirring for 60 h. At this time the reaction was allowed to cool to RT partitioned between EtOAc and 1N aqueous HCl. The aqueous fraction was extracted with EtOAc and the combined organics washed with saturated aqueous $Na_2CO_3$, brine, before being dried over $Na_2SO_4$, filtered and evaporated in vacuo. Purification was by flash chromatography on silica gel (4:6) EtOAc/PE to afford the title compound (24%).

$^1$H NMR (300 MHz, DMSO-$d_6$, 300 K) δ 1.4 (s, 9H), 3.03-3.05 (m, 4H), 3.40-3.45 (m, 4H), 6.83 (d, J 8.7, 2H), 6.92 (d, J 8.7, 2H), 7.58 (d, J 8.7, 2H), 7.81 (d, J 8.7, 2H), 9.78 (s, 1H), 10.0 (s, 1H); MS ($ES^-$) m/z 396 $(M-H)^-$.

The following tables show additional examples:

TABLE 1

| Example | Name | m/z ($ES^+$) | Synthetic procedure |
|---|---|---|---|
| 101 | tert-butyl 4-(4-{[(4-hydroxyphenyl)amino]carbonyl}phenyl)piperazine-1-carboxylate | 398 | A |
| 102 | tert-butyl 4-(4-{[(4-bromophenyl)amino]carbonyl}phenyl)piperazine-1-carboxylate | 461 | A |
| 103 | tert-butyl 4-(4-{[(3-bromophenyl)amino]carbonyl}phenyl)piperazine-1-carboxylate | 461 | A |
| 104 | tert-butyl 4-{4-[({3-[(1E)-3-methoxy-3-oxoprop-1-en-1-yl]phenyl}amino)carbonyl]phenyl}piperazine-1-carboxylate | 466 | A |
| 105 | tert-butyl 4-[4-({[4-(methoxycarbonyl)phenyl]amino}carbonyl)phenyl]piperazine-1-carboxylate | 440 | A |
| 106 | methyl 1-benzoyl-5-({4-[4-(tert-butoxycarbonyl)piperazin-1-yl]benzoyl}amino)indoline-2-carboxylate | 584 | A |
| 107 | tert-butyl 4-(4-{[(4-hydroxy-3-iodophenyl)amino]carbonyl}phenyl)piperazine-1-carboxylate | 524 | A |
| 108 | tert-butyl 4-(4-{[(3-acetylphenyl)amino]carbonyl}phenyl)piperazine-1-carboxylate | 424 | B |
| 109 | tert-butyl 4-[4-({[2-(4-hydroxyphenyl)ethyl]amino}carbonyl)phenyl]piperazine-1-carboxylate | 426 | B |
| 110 | tert-butyl 4-(4-{[(4-cyanophenyl)amino]carbonyl}phenyl)piperazine-1-carboxylate | 407 | B |
| 111 | tert-butyl 4-{4-[(1,3-benzothiazol-2-ylamino)carbonyl]phenyl}piperazine-1-carboxylate | 439 | B |
| 112 | tert-butyl 4-(4-{[(4-benzoylphenyl)amino]carbonyl}phenyl)piperazine-1-carboxylate | 486 | B |
| 113 | tert-butyl 4-{4-[(biphenyl-4-ylamino)carbonyl]phenyl}piperazine-1-carboxylate | 458 | B |
| 114 | tert-butyl 4-[4-({[4-(dimethylamino)phenyl]amino}carbonyl)phenyl]piperazine-1-carboxylate | 425 | B |
| 115 | tert-butyl 4-(4-{[(4-vinylphenyl)amino]carbonyl}phenyl)piperazine-1-carboxylate | 408 | B |
| 116 | tert-butyl 4-{4-[({4-[(E)-2-(4-hydroxyphenyl)vinyl]phenyl}amino)carbonyl]phenyl}piperazine-1-carboxylate | 500 | B |
| 117 | tert-butyl 4-[4-({[3,5-bis(trifluoromethyl)phenyl]amino}carbonyl)phenyl]piperazine-1-carboxylate | 518 | B |
| 118 | tert-butyl 4-[4-({[3-(benzyloxy)phenyl]amino}carbonyl)phenyl]piperazine-1-carboxylate | 488 | B |
| 119 | tert-butyl 4-{4-[(1H-indazol-6-ylamino)carbonyl]phenyl}piperazine-1-carboxylate | 422 | B |
| 120 | tert-butyl 4-{4-[(1H-indazol-5-ylamino)carbonyl]phenyl}piperazine-1-carboxylate | 422 | B |
| 121 | tert-butyl 4-{4-[(1-naphthylamino)carbonyl]phenyl}piperazine-1-carboxylate | 432 | B |
| 122 | tert-butyl 4-(4-{[(5-hydroxy-1-naphthyl)amino]carbonyl}phenyl)piperazine-1-carboxylate | 448 | B |
| 123 | tert-butyl 4-[4-({[4-(acetyloxy)phenyl]amino}carbonyl)phenyl]piperazine-1-carboxylate | 440 | C |

TABLE 2

| Example | Name | m/z (ES+) | Synthetic procedure |
|---|---|---|---|
| 201 | isobutyl 4-(4-{[(4-hydroxyphenyl)amino]carbonyl}phenyl)piperazine-1-carboxylate | 398 | C |
| 202 | ethyl 4-(4-{[(4-hydroxyphenyl)amino]carbonyl}phenyl)piperazine-1-carboxylate | 370 | C |
| 203 | 2,2-dimethylpropyl 4-(4-{[(4-hydroxyphenyl)amino]carbonyl}phenyl)piperazine-1-carboxylate | 412 | C |
| 204 | allyl 4-(4-{[(4-hydroxyphenyl)amino]carbonyl}phenyl)piperazine-1-carboxylate | 382 | C |
| 205 | phenyl 4-(4-{[(4-hydroxyphenyl)amino]carbonyl}phenyl)piperazine-1-carboxylate | 418 | C |
| 206 | 4-chlorobenzyl 4-(4-{[(4-hydroxyphenyl)amino]carbonyl}phenyl)piperazine-1-carboxylate | 466 | C |
| 207 | 2-naphthylmethyl 4-(4-{[(4-hydroxyphenyl)amino]carbonyl}phenyl)piperazine-1-carboxylate | 482 | C |
| 208 | 2,5-dichlorobenzyl 4-(4-{[(4-hydroxyphenyl)amino]carbonyl}phenyl)piperazine-1-carboxylate | 500 | C |
| 209 | 5-bromo-2-methoxybenzyl 4-(4-{[(4-hydroxyphenyl)amino]carbonyl}phenyl)piperazine-1-carboxylate | 540 | C |
| 210 | 3-{[(tert-butoxycarbonyl)amino]methyl}benzyl 4-(4-{[(4-hydroxyphenyl)amino]carbonyl}phenyl)piperazine-1-carboxylate | 561 | C |
| 211 | 2-methylbenzyl 4-(4-{[(4-hydroxyphenyl)amino]carbonyl}phenyl)piperazine-1-carboxylate | 446 | C |
| 212 | 2-methoxybenzyl 4-(4-{[(4-hydroxyphenyl)amino]carbonyl}phenyl)piperazine-1-carboxylate | 462 | C |
| 213 | 3-methoxybenzyl 4-(4-{[(4-hydroxyphenyl)amino]carbonyl}phenyl)piperazine-1-carboxylate | 462 | C |
| 214 | 2,3-dimethoxybenzyl 4-(4-{[(4-hydroxyphenyl)amino]carbonyl}phenyl)piperazine-1-carboxylate | 492 | C |
| 215 | 1-naphthylmethyl 4-(4-{[(4-hydroxyphenyl)amino]carbonyl}phenyl)piperazine-1-carboxylate | 482 | C |
| 216 | benzyl 4-(4-{[(4-hydroxyphenyl)amino]carbonyl}phenyl)piperazine-1-carboxylate | 432 | C |

TABLE 3

| Example | Name | m/z (ES+) | Synthetic procedure |
|---|---|---|---|
| 301 | N-(2-chlorobenzyl)-4-(4-{[(4-hydroxyphenyl)amino]carbonyl}phenyl)piperazine-1-carboxamide | 465 | C |
| 302 | N-(tert-butyl)-4-(4-{[(4-hydroxyphenyl)amino]carbonyl}phenyl)piperazine-1-carboxamide | 397 | C |
| 303 | 4-(4-{[(4-hydroxyphenyl)amino]carbonyl}phenyl)-N-(4-methoxybenzyl)piperazine-1-carboxamide | 461 | C |
| 304 | N-benzyl-4-(4-{[(4-hydroxyphenyl)amino]carbonyl}phenyl)piperazine-1-carboxamide | 431 | C |
| 305 | N-butyl-4-(4-{[(4-hydroxyphenyl)amino]carbonyl}phenyl)piperazine-1-carboxamide | 397 | C |
| 306 | 4-(4-{[(4-hydroxyphenyl) amino]carbonyl}phenyl)-N-[(1R)-1-phenylethyl] piperazine-1-carboxamide | 445 | C |
| 307 | N-biphenyl-2-yl-4-(4-{[(4-hydroxyphenyl)amino]carbonyl}phenyl)piperazine-1-carboxamide | 493 | C |
| 308 | 4-(4-{[(4-hydroxyphenyl) amino]carbonyl}phenyl)-N-phenylpiperazine-1-carboxamide | 417 | C |
| 309 | N-(4-fluorobenzyl)-4-(4-{[(4-hydroxyphenyl)amino]carbonyl}phenyl)piperazine-1-carboxamide | 449 | C |
| 310 | 4-(4-{[(4-hydroxyphenyl) amino]carbonyl}phenyl)-N-[(1R)-1-(1-naphthyl)ethyl] piperazine-1-carboxamide | 495 | C |
| 311 | 4-(4-{[(4-hydroxyphenyl) amino]carbonyl}phenyl)-N-(4-methylbenzyl)piperazine-1-carboxamide | 445 | C |
| 312 | 4-(4-{[(4-hydroxyphenyl) amino]carbonyl}phenyl)-N-(3-methylbenzyl)piperazine-1-carboxamide | 445 | C |

TABLE 4

| Example | Name | m/z (ES+) | Synthetic procedure |
|---|---|---|---|
| 401 | 4-[4-(cyclohexylcarbonyl)piperazin-1-yl]-N-(4-hydroxyphenyl)benzamide | 408 | C |
| 402 | N-(4-hydroxyphenyl)-4-[4-(3-phenylpropanoyl)piperazin-1-yl]benzamide | 430 | C |

TABLE 4-continued

| Example | Name | m/z (ES+) | Synthetic procedure |
|---|---|---|---|
| 403 | 4-[4-(2,2-dimethylpropanoyl)piperazin-1-yl]-N-(4-hydroxyphenyl)benzamide | 382 | C |
| 404 | 4-({4-[4-(2,2-dimethylpropanoyl)piperazin-1-yl]benzoyl}amino)phenyl acetate | 424 | C |
| 405 | N-(4-hydroxyphenyl)-4-{4-[4-(trifluoromethyl)benzoyl]piperazin-1-yl}benzamide | 470 | C |
| 406 | 4-(4-benzoylpiperazin-1-yl)-N-(4-hydroxyphenyl)benzamide | 402 | C |
| 407 | 4-[4-(3-cyclopentylpropanoyl)piperazin-1-yl]-N-(4-hydroxyphenyl)benzamide | 422 | C |
| 408 | 4-[4-(3-cyanobenzoyl)piperazin-1-yl]-N-(4-hydroxyphenyl)benzamide | 527 | C |
| 409 | N-(4-hydroxyphenyl)-4-(4-{(2E)-3-[3-(trifluoromethyl)phenyl]prop-2-enoyl}piperazin-1-yl)benzamide | 496 | C |
| 410 | N-(4-hydroxyphenyl)-4-[4-(1-naphthoyl)piperazin-1-yl]benzamide | 452 | C |

TABLE 5

| Example | Name | m/z (ES+) | Synthetic procedure |
|---|---|---|---|
| 501 | N-(4-hydroxyphenyl)-4-[4-(1-naphthylsulfonyl)piperazin-1-yl]benzamide | 488 | C |
| 502 | N-(4-hydroxyphenyl)-4-{4-[(4-methoxyphenyl)sulfonyl]piperazin-1-yl}benzamide | 468 | C |
| 503 | N-(4-hydroxyphenyl)-4-(4-{[(E)-2-phenylvinyl]sulfonyl}piperazin-1-yl)benzamide | 464 | C |
| 504 | N-(4-hydroxyphenyl)-4-{4-[(5-pyridin-2-yl-2-thienyl)sulfonyl]piperazin-1-yl}benzamide | 521 | C |

TABLE 6

| Example | Name | m/z (ES+) | Synthetic procedure |
|---|---|---|---|
| 601 | tert-butyl 1-(4-{[(4-hydroxyphenyl)amino]carbonyl}phenyl)piperidine-4-carboxylate | 397 | D |
| 602 | tert-butyl 4-(4-{[(4-hydroxyphenyl)amino]carbonyl}phenyl)piperidine-1-carboxylate | 397 | A |
| 603 | tert-butyl 4-{4-[(4-hydroxybenzoyl)amino]phenyl}piperazine-1-carboxylate | 398 | E |
| 604 | tert-butyl 4-{4-[(4-aminobenzoyl)amino]phenyl}piperazine-1-carboxylate | 397 | E |
| 605 | tert-butyl 4-(3-hydroxy-4-{[(4-hydroxyphenyl)amino]carbonyl}phenyl)piperazine-1-carboxylate | 414 | A |

The invention claimed is:

1. The compound of formula (Ia) or a pharmaceutically acceptable salt thereof:

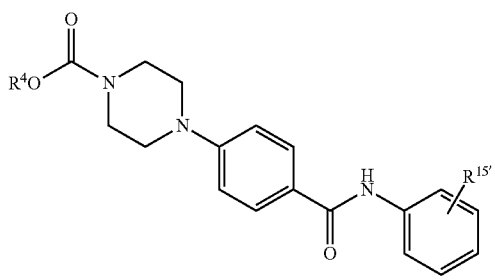

(Ia)

wherein

R$^4$ is C$_{1-6}$alkyl, C$_{2-6}$alkenyl, C$_{2-6}$alkynyl, (CH$_2$)$_{0-3}$C$_{3-8}$cycloalkyl, C$_{1-6}$alkoxy, (CH$_2$)$_{0-3}$aryl, (CH)$_2$aryl, (C$_2$)$_{0-3}$Oaryl, (CH$_2$)$_{0-3}$heteroaryl and (CH$_2$)$_{0-3}$Oheteroaryl, optionally substituted by hydroxy, halogen, CN, CF$_3$, C$_{1-4}$alkyl, C$_{1-4}$alkoxy, (CH$_2$)$_{0-3}$NR$^{11}$C(O)OR$^{12}$, (CH$_2$)$_{0-3}$ aryl or (CH$_2$)$_{0-3}$heteroaryl, where R$^{11}$ and R$^{12}$ are each independently hydrogen or C$_{1-6}$alkyl; and R$^{15'}$ is CN, CF$_3$, C$_{2-4}$alkenyl, phenyl, OBn, C(O)C$_{1-4}$alkyl, or C(O)phenyl.

2. The compound as claimed in claim 1, wherein R$^4$ is C$_{1-6}$alkyl, aryl or benzyl, optionally substituted by one or two substituents chosen from fluorine, chlorine, bromine, CN, methyl, methoxy and CF$_3$.

3. The compound as claimed in claim 1, wherein R$^4$ is C$_{1-6}$alkyl, C$_{2-6}$alkenyl or (CH$_2$)$_{0-3}$aryl, optionally substituted by one or two substituents selected from halogen, C$_{1-4}$alkyl, C$_{1-4}$alkoxy and —CH$_2$NHC(O)OC$_{1-4}$alkyl.

4. A pharmaceutical composition comprising a compound as claimed in claim 1 in association with a pharmaceutically acceptable carrier.

5. A method of preparation of a pharmaceutical composition by admixing at least one compound as claimed in claim 1 with one or more pharmaceutically acceptable adjuvants, diluents or carriers and/or with one or more other therapeutically or prophylactically active agents.

6. A method of treating HCV infection by administering an effective amount of a compound of formula (I) or a pharmaceutically acceptable salt thereof:

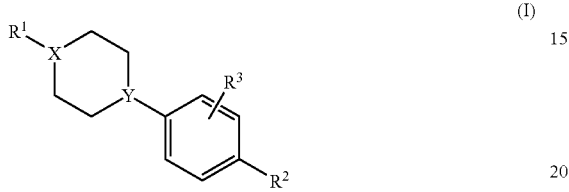

(I)

wherein
X and Y are independently N;
$R^1$ is $C(O)OR^4$, $C(O)NR^5R^6$, or $C(O)R^7$;
$R^2$ is $C(O)NR^9R^{10}$ or $NR^9C(O)R^{10}$;
$R^3$ is absent or selected from halogen, hydroxy, $C_{1-6}$alkyl and $C_{1-6}$alkoxy;
$R^5$ and $R^9$ are each independently hydrogen, $C_{1-6}$alkyl or $C_{3-8}$cycloalkyl;
$R^4$, $R^6$, $R^7$ and $R^8$ are each independently selected from $C_{1-6}$alkyl, $C_{2-6}$alkenyl, $C_{2-6}$alkynyl, $(CH_2)_{0-3}C_{3-8}$cycloalkyl, $C_{1-6}$alkoxy, $(CH_2)_{0-3}$aryl, $(CH)_2$aryl, $(CH_2)_{0-3}$Oaryl, $(CH_2)_{0-3}$heteroaryl and $(CH_2)_{0-3}$Oheteroaryl, optionally substituted by hydroxy, halogen, CN, $CF_3$, $C_{1-4}$alkyl, $C_{1-4}$alkoxy, $(CH_2)_{0-3}NR^{11}C(O)OR^{12}$, $(CH_2)_{0-3}$aryl or $(CH_2)_{0-3}$heteroaryl,
where $R^{11}$ and $R^{12}$ are each independently hydrogen or $C_{1-6}$alkyl;
$R^{10}$ is $(CH_2)_{0-3}$aryl or $(CH_2)_{0-3}$heteroaryl, optionally substituted by halogen, CN, $CF_3$, $C_{1-4}$alkyl, $C_{2-4}$alkenyl, $OR^{13}$, $C(O)R^{13}$, $C(O)OR^{13}$, aryl, $(CH)_2$aryl, $(CH)_2C(O)OR^{13}$ or $NR^{13}R^{14}$,
where $R^{13}$ and $R^{14}$ are each independently hydrogen, $C_{1-4}$alkyl or $(CH_2)_{0-3}$aryl,
and where the optional substituent is further optionally substituted by hydroxy or halogen,
and $R^{10}$ may further be fused to a 5- or 6-membered ring, which ring may be partially or fully unsaturated and which ring may contain one or two N atoms, said ring being optionally substituted by hydroxy, halogen, $C_{1-4}$alkyl, $C_{1-4}$alkoxy, $C(O)R^{15}$ and $C(O)OR^{15}$,
where $R^{15}$ is $C_{1-4}$alkyl or aryl; with the proviso that the compound of formula (I) is not:
tert-butyl4-(4-{[(4-hydroxyphenyl)amino]carbonyl}phenyl)piperazine-1-carboxylate,
tert-butyl4-(4-{[(4-bromophenyl)amino]carbonyl}phenyl)piperazine-1-carboxylate,
tert-butyl4-(4-{[(3-bromophenyl)amino]carbonyl}phenyl)piperazine-1-carboxylate,
tert-butyl4-{4-[({3-[(1E)-3-methoxy-3-oxoprop-1-en-1-yl]phenyl}amino)carbonyl]phenyl}piperazine-1-carboxylate,
tert-butyl4-{4-[(4-hydroxybenzoyl)amino]phenyl}piperazine-1-carboxylate, or tert-butyl4-{4-[(4-aminobenzoyl)amino]phenyl}piperazine-1-carboxylate.

7. A method of treating an illness due to hepatitis C virus, the method comprising administering to a human subject suffering from the illness a therapeutically effective amount of a compound of formula (I) or a pharmaceutically acceptable salt thereof:

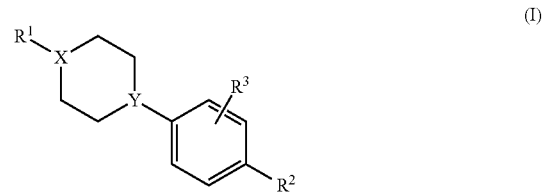

(I)

wherein
X and Y are independently N;
$R^1$ is $C(O)OR^4$, $C(O)NR^5R^6$, or $C(O)R^7$;
$R^2$ is $C(O)NR^9R^{10}$ or $NR^9C(O)R^{10}$;
$R^3$ is absent or selected from halogen, hydroxy, $C_{1-6}$alkyl and $C_{1-6}$alkoxy;
$R^5$ and $R^9$ are each independently hydrogen, $C_{1-6}$alkyl or $C_{3-8}$cycloalkyl;
$R^4$, $R^6$, $R^7$ and $R^8$ are each independently selected from $C_{1-6}$alkyl, $C_{2-6}$alkenyl, $C_{2-6}$alkynyl, $(CH_2)_{0-3}C_{3-8}$cycloalkyl, $C_{1-6}$alkoxy, $(CH_2)_{0-3}$aryl, $(CH)_2$aryl, $(CH_2)_{0-3}$Oaryl, $(CH_2)_{0-3}$heteroaryl and $(CH_2)_{0-3}$Oheteroaryl, optionally substituted by hydroxy, halogen, CN, $CF_3$, $C_{1-4}$alkyl, $C_{1-4}$alkoxy, $(CH_2)_{0-3}NR^{11}C(O)OR^{12}$, $(CH_2)_{0-3}$aryl or $(CH_2)_{0-3}$heteroaryl,
where $R^{11}$ and $R^{12}$ are each independently hydrogen or $C_{1-6}$alkyl;
$R^{10}$ is $(CH_2)_{0-3}$aryl or $(CH_2)_{0-3}$heteroaryl, optionally substituted by halogen, CN, $CF_3$, $C_{1-4}$alkyl, $C_{2-4}$alkenyl, $OR^{13}$, $C(O)R^{13}$, $C(O)OR^{13}$, aryl, $(CH)_2$aryl, $(CH)_2C(O)OR^{13}$ or $NR^{13}R^{14}$,
where $R^{13}$ and $R^{14}$ are each independently hydrogen, $C_{1-4}$alkyl or $(CH_2)_{0-3}$aryl,
and where the optional substituent is further optionally substituted by hydroxy or halogen,
and $R^{10}$ may further be fused to a 5- or 6-membered ring, which ring may be partially or fully unsaturated and which ring may contain one or two N atoms, said ring being optionally substituted by hydroxy, halogen, $C_{1-4}$alkyl, $C_{1-4}$alkoxy, $C(O)R^{15}$ and $C(O)OR^{15}$,
where $R^{15}$ is $C_{1-4}$alkyl or aryl, with the proviso that the compound of formula (I) is not:
tent-butyl4-(4-{[(4-hydroxyphenyl)amino]carbonyl}phenyl)piperazine-1-carboxylate,
tert-butyl4-(4-{[(4-bromophenyl)amino]carbonyl}phenyl)piperazine-1-carboxylate,
tent-butyl4-(4-{[(3-bromophenyl)amino]carbonyl}phenyl)piperazine-1-carboxylate,
tent-butyl4- {4- [({3-[(1E)-3-methoxy-3-oxoprop-1-en-1-yl]phenyl}amino)carbonyl]phenyl}piperazine-1-carboxylate,
tert-butyl4-{4-[(4-hydroxybenzoyl)amino]phenyl}piperazine-1-carboxylate, or
tert-butyl4-{4-[(4-aminobenzoyl)amino]phenyl}piperazine-1-carboxylate.

* * * * *